US010153144B2

(12) United States Patent
Sanford et al.

(10) Patent No.: US 10,153,144 B2
(45) Date of Patent: *Dec. 11, 2018

(54) IMAGING SPECTROMETER

(71) Applicant: The United States of America, as Represented by the Secretary of Commerce, Washington, DC (US)

(72) Inventors: Norman A. Sanford, Boulder, CO (US); Ann Chiaramonti Debay, Louisville, CO (US)

(73) Assignee: THE UNITED STATES OF AMERICA, AS REPRESENED BY THE SECRETARY OF COMMERCE, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/632,959

(22) Filed: Jun. 26, 2017

(65) Prior Publication Data

US 2017/0301526 A1    Oct. 19, 2017

Related U.S. Application Data

(63) Continuation of application No. 15/226,307, filed on Aug. 2, 2016, now Pat. No. 9,899,197.

(Continued)

(51) Int. Cl.
*H01J 49/00*     (2006.01)
*H01J 49/40*     (2006.01)
*H01J 49/16*     (2006.01)
*G01N 23/046*   (2018.01)
*H05G 2/00*      (2006.01)

(52) U.S. Cl.
CPC ........ *H01J 49/0004* (2013.01); *G01N 23/046* (2013.01); *H01J 49/0031* (2013.01); *H01J 49/161* (2013.01); *H01J 49/40* (2013.01); *H01J 49/004* (2013.01); *H05G 2/008* (2013.01)

(58) Field of Classification Search
CPC .. H01J 49/0059; H01J 49/0027; H01J 49/025; G01N 23/046; G21K 7/00; G01T 1/29
USPC .... 250/306, 307, 308, 309, 310, 311, 493.1, 250/492.1, 492.2, 492.3, 494.1, 503.1, 250/504 R
See application file for complete search history.

(56) References Cited

U.S. PATENT DOCUMENTS

2013/0277552 A1    10/2013   Nanri et al.

OTHER PUBLICATIONS

Schreiber, D.K., et al., Applicability of post-ionization theory to laser-assisted field evaporation of magnetite, Applied Physics Letters, 2014, 24406, 105.

(Continued)

*Primary Examiner* — Nicole Ippolito
*Assistant Examiner* — Hanway Chang
(74) *Attorney, Agent, or Firm* — Office of Chief Counsel for National Institute of Standards and Technology

(57) ABSTRACT

A extreme ultraviolet (EUV) imaging spectrometer includes: a radiation source to: produce EUV radiation; subject a sample to the EUV radiation; photoionize a plurality of atoms of the sample; and form photoions from the atoms subject to photoionization by the EUV radiation, the photoions being field evaporated from the sample in response to the sample being subjected to the EUV radiation; and an ion detector to detect the photoions: as a function of a time-of-arrival of the photoions at the ion detector after the sample is subjected to the EUV radiation; or as a function of a position of the photoions at the ion detector.

14 Claims, 18 Drawing Sheets

Related U.S. Application Data

(60) Provisional application No. 62/212,857, filed on Sep. 1, 2015.

(56) References Cited

OTHER PUBLICATIONS

Gault, B., et al., Behavior of molecules and molecular ions near a field emitter, New Journal of Physics, 2016, 18.

Diercks, D.R., et al., Atom probe tomography evaporation behavior of C-axis GaN nanowires: Crystallographic, stoichimetric, and detection efficiency aspects, Journal of Applied Physics, 2013, 184903, 114.

Sanford, N.A., et al., Laser-assisted atom probe tomography of MBE grown GaN nanowire heterostructures, Physics Status Solidi C, 2014, 608-612, 11.

Sanford, N.A., et al., Laser-assisted atom probe tomography of Ti/TiN films deposited on Si, Micron, 2017, 53-65, 94.

Kusnetsov, I., et al., Three-dimensional nanoscale molecular imaging by extreme ultraviolet laser ablation mass spectrometry, 2015, Nature Communications 6, Article 6944.

IMAGING SPECTROMETER

CROSS REFERENCE TO RELATED APPLICATIONS

This application claims the benefit of U.S. Provisional Patent Application Ser. No. 62/212,857, filed Sep. 1, 2015, the disclosure of which is incorporated herein by reference in its entirety. This application is a continuation-in-part application of application Ser. No. 15/266,307, filed Aug. 2, 2016.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is an imaging spectrometer comprising: a radiation source to: produce EUV radiation; subject a sample to the EUV radiation; photoionize a plurality of atoms of the sample; and form photoions from the atoms subject to photoionization by the EUV radiation, the photoions being radioactively field evaporated from the sample in response to the sample being subjected to the EUV radiation in a presence of an external electric field; an ion detector to detect the photoions: as a function of a time-of-arrival of the photoions at the ion detector after the sample is subjected to the EUV radiation in the presence of an external electric field; or as a function of a position of the photoions at the ion detector.

Also disclosed is a process for performing extreme ultraviolet (EUV) imaging of a sample, the process comprising: producing, by a radiation source, EUV radiation; subjecting the sample to the EUV radiation; photoionizing a plurality of atoms of the sample; forming photoions from the atoms subject to photoionization by the EUV radiation; field evaporating the photoions from the sample in response to the sample being subjected to the EUV radiation in the presence of an external electric field; detecting, by an ion detector, the photoions: as a function of a time-of-arrival of the photoions at the ion detector after the sample is subjected to the EUV radiation; or as a function of a position of the photoions at the ion detector; and acquiring, by an analyzer, data from the ion detector to image the sample.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a hybrid extreme ultraviolet (EUV) or an EUV imaging spectrometer herein acquires quantitative three-dimensional chemical maps of a sample that can include hard matter or soft matter. Advantageously, the hybrid EUV imaging spectrometer and EUV imaging spectrometer have sub-nanometer spatial resolution for an elemental constituent of a sample subjected to EUV radiation or primary electrons.

Figure 1:
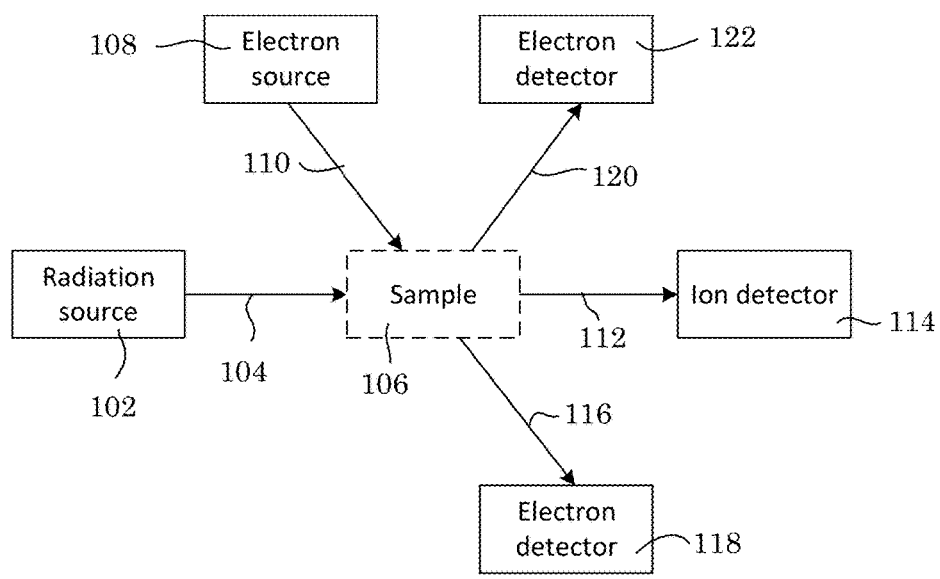
FIG. 1 shows a hybrid extreme ultraviolet (EUV) imaging spectrometer.

In an embodiment, with reference to FIG. 1, hybrid extreme ultraviolet (EUV) imaging spectrometer 100 includes radiation source 102 to produce EUV radiation 104 and is configured to subject sample 106 to pulsed EUV radiation 104, to photoionize a plurality of atoms of sample 106, and to form photoions 112 from the atoms subject to single photoionization by EUV radiation 104. Photoions 112 are radioactively field evaporated from sample 106 in response to sample 106 being subjected to EUV radiation 104. Also, hybrid EUV imaging spectrometer 100 includes ion detector 114 to detect photoions 112 as a function of a time-of-arrival of photoions 112 at ion detector 114 after sample 106 is subjected to EUV radiation 104, or as a function of a position of photoions 112 at ion detector 114. Electron source 108 produces a plurality of primary electrons 110 to subject sample 106 to primary electrons 110 and to form scattered electrons (116 or 120) from sample 106 in response to sample 106 being subjected to primary electrons 110. Electron detector (118 or 122) detects scattered electrons (116 or 120, respectively) as a function of a time-of-arrival of scattered electrons (116 or 120, respectively) at electron detector (118 or 122, respectively) after sample 106 is subjected to EUV radiation 104 or primary electrons 110, or as a function of a position of scattered electrons (116 or 120) at electron detector (118 or 122).

As used herein, "radioactively field evaporated" (and variants thereof, e.g., radiative desorption and the like) refers to photoions removed from sample 106 in response to sample 106 being subjected to EUV radiation 104 in a presence of an electric field provided by extraction electrode 150 or an external electric field. It should be appreciated that ionization of atoms of sample 106 and desorption of such photoions in a presence of the electric field provided by extraction electrode 150 or an external electric field can occur when using lower energy, a longer wavelength radiation (e.g., ultraviolet or visible radiation) as compared to EUV radiation 104. This lower energy ionization process can produce multiply charged photoions and local heating of a sample. Subjecting sample 106 to EUV radiation 104 produces photoions 112 that are substantially radioactively field evaporated from sample 106. Without wishing to be bound by theory, it is believed that a contribution to desorption of photoions 112 from sample 106 occurs in a presence of EUV radiation 104 due to radiative desorption in an absence of thermal desorption and in an absence of production of multiply charged photoions, wherein photoions 112 are singly charged, e.g., ($Ni^+$, $C^+$, $H_2O^+$, $C_2H_3^+$, and the like).

Figure 2:
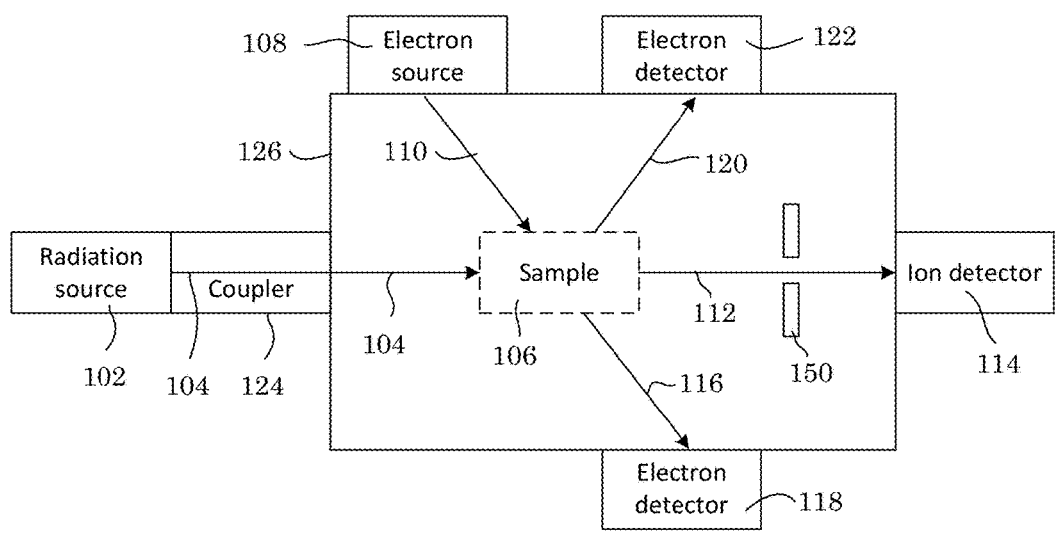
FIG. 2 shows a hybrid extreme ultraviolet imaging spectrometer.

In an embodiment, with reference to FIG. 2, hybrid EUV imaging spectrometer 100 includes chamber 126 (e.g., a vacuum chamber) in which is disposed sample 106. Ion optics 150 (e.g., an ion extraction electrode) can be interposed between radiation source 102 and ion detector 114, specifically interposed between sample 106 and ion detector 114 to extract photoions 112 released from sample 106 and to communicate photoions 112 to ion detector 114. According to an embodiment, extraction electrode 150 is disposed proximate to sample 106 and interposed between sample 106 and ion detector 114, wherein extraction electrode 150 includes an aperture to transmit photoions 112 from sample 106 to ion detector 114.

Coupler 124 is interposed between radiation source 102 and chamber 126 to optically coupled radiation source 102 to sample 106 disposed in chamber 126. In this manner, EUV radiation 104 can be produced and transmitted without negatively impacting affluence of EUV radiation 104 such as by absorption of atmospheric gases before EUV radiation 104 interacts with sample 106. Here, chamber 126 provides a platform to dispose and arrange sample 106 relative to radiation source 102, electron source 108, and detectors 114, 118, 122. Further, chamber 126 provides a selected environmental condition for sample 106, EUV radiation 104, primary electrons 110, photoions 112, and scattered electrons 116, 120. The selected environmental condition can include temperature, pressure, gas composition, ultra-high vacuum, and the like.

Figure 3:
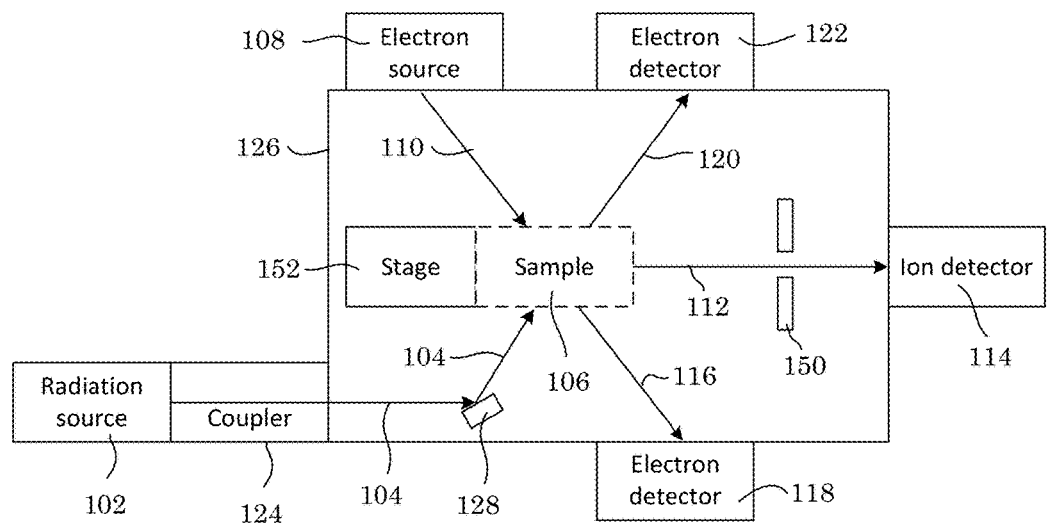
FIG. 3 shows a hybrid extreme ultraviolet imaging spectrometer.

In an embodiment, with reference to FIG. 3, hybrid EUV imaging spectrometer 100 includes EUV optic 128 disposed in chamber 126 to communicate and to selectively direct EUV radiation 104 from a radiation source 102 to sample 106. Stage 152 disposed in chamber 126 receives sample 106, wherein sample 106 can be mounted on stage 152. A position of sample 106 relative to components (e.g., EUV optic 128 and ion optics 150) of hybrid EUV imaging spectrometer 100 can be controlled statically or dynamically by stage 152.

Figure 4:
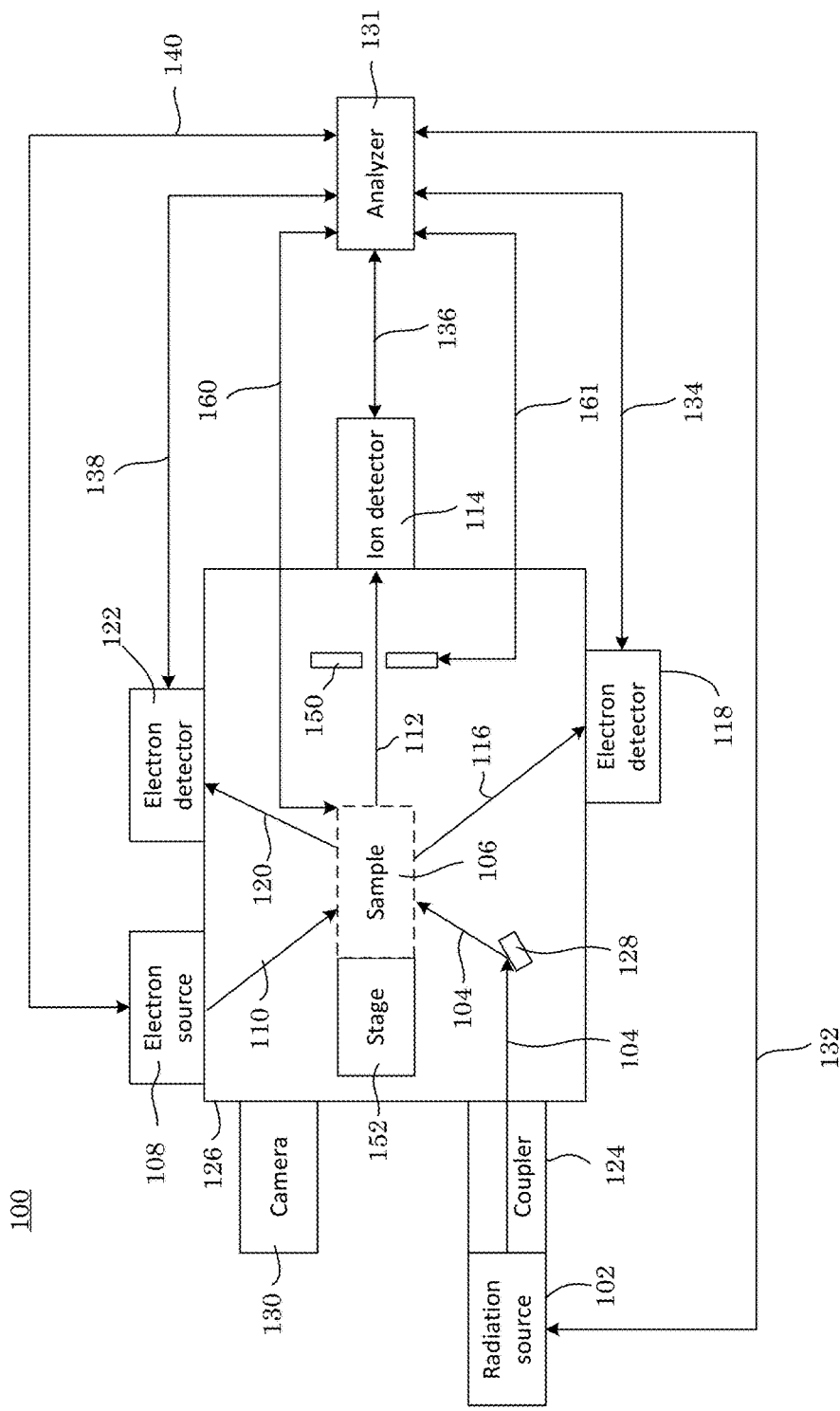
FIG. 4 shows a hybrid extreme ultraviolet imaging spectrometer.

According to an embodiment, with reference to FIG. 4, hybrid EUV imaging spectrometer 100 includes analyzer 131 to acquire data from ion detector 114 and electron detectors (118, 122), to continuously analyze the data for reconstruction of a shape of sample 106 and a chemical composition of sample 106, and to determine a tomographic shape and composition of sample 106. Here, analyzer 131 can be in electrical communication with radiation source 102 to receive EUV source data 132 (e.g., a pulse length, duty cycle, power, repetition rate, wavelength, and the like of EUV radiation 104) or to control radiation source 102. Likewise, analyzer 131 can be in electrical communication with electron detector 118 to receive electron data 134 (e.g., a time-of-arrival, diffraction pattern, position of arrival on detector 118, transmission electron micrograph, energy, and the like of scattered electrons 116) or control operation of electron detector 118 (e.g., bias voltage, capture time, and the like). Analyzer 131 can be in electrical communication with electron detector 122 to receive electron data 138 (e.g., a time-of-arrival, position of arrival on detector 118, energy, scanning electron micrograph, and the like of scattered electrons 116) or to control electron detector 122. Analyzer 131 can be in electrical communication with electron source 108 to receive electron source data 140 (e.g., energy, spatial distribution, flux, and the like of primary electrons 110) or to control electron source 108. Analyzer 131 can be in electrical communication with ion detector 114 to receive ion data 136 (e.g., a time-of-arrival, position of arrival on detector 114, energy, two-dimensional image, and the like of photoions 112) or to control ion detector 114 (e.g., detection on time, bias voltage, and the like). Analyzer 131 can be in electrical communication with sample 106 to receive sample data 160 (e.g., temperature, voltage, and the like of sample 106) or to control sample 106 (or stage 152) (e.g., position, bias voltage, and the like). Similarly, analyzer 131 can be in electrical communication with extraction electrode 150 to receive extraction electrode data 161 (e.g., voltage and the like of extraction electrode 150) or to control extraction electrode 150 (e.g., bias voltage and the like).

Figure 5:
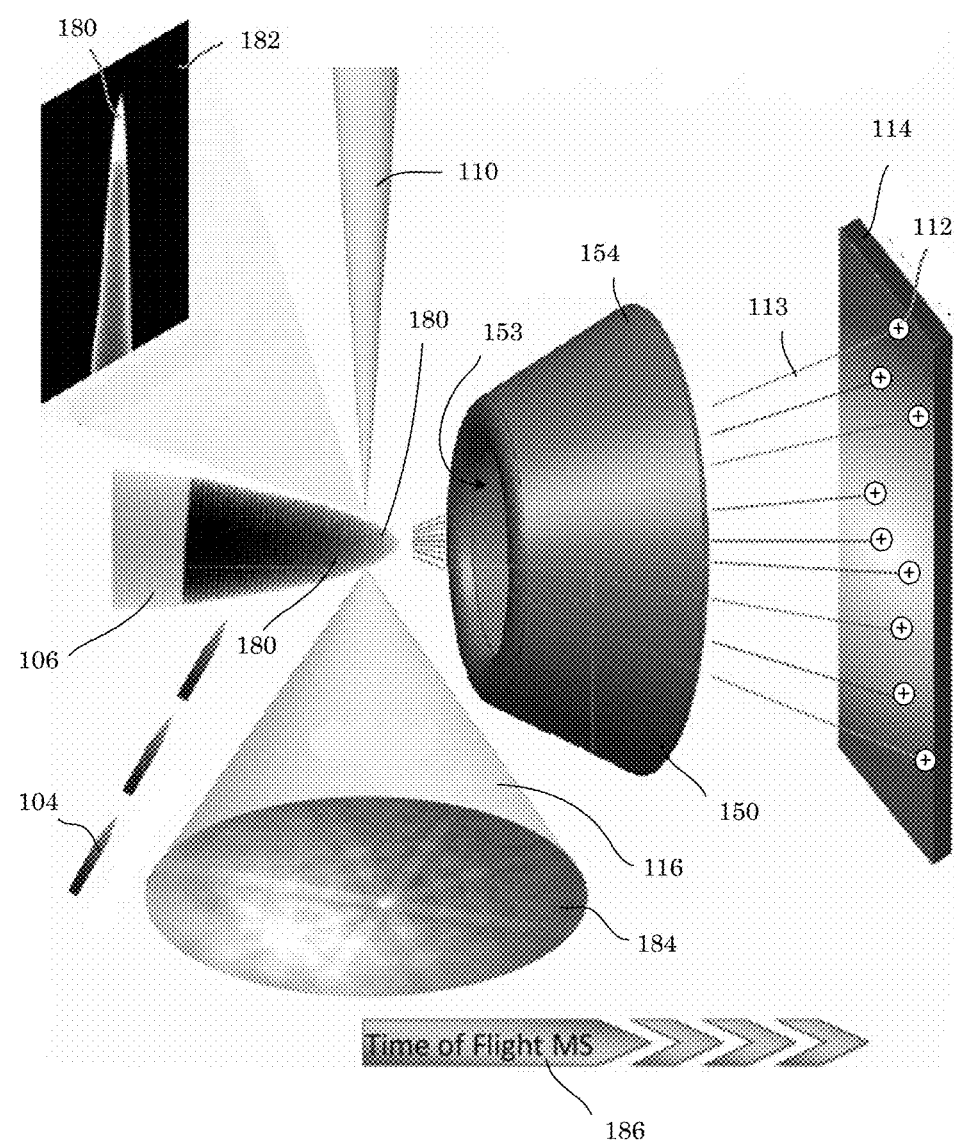
FIG. 5 shows production of photoions and electron images by subjecting a sample to primary electrons and EUV radiation.

Although not shown explicitly in FIG. 1, FIG. 2, FIG. 3, FIG. 4, or FIG. 5, hybrid EUV imaging spectrometer 100 can include hardware, instrumentation or software for a fully functional atom probe tomograph. It is contemplated that hardware can include high voltage power supply, timing electronics, and position-sensitive 2D detectors, sample shape and composition reconstruction algorithms, and the like that can be integrated with EUV radiation source 102, EUV optic 128, and other components (e.g., detectors (122, 118, 114) of hybrid EUV imaging spectrometer 100 to provide operability of hybrid EUV imaging spectrometer 100 as shown in FIG. 5. Here, sample 106 having tip 180 is subjected to pulsed EUV radiation 104 such that photoions 112 are produced from tip 180 and propagate from sample 106 two ion detector 114 along ion trajectory 113. Photoions 112 are communicated through aperture 153 to traverse extraction electrode 150 and impact ion detector 114 (e.g., a two-dimensional particle detector) in a pattern, wherein the position of photoions 112 in the pattern on ion detector 114 depends upon a position of the atoms that were photoionized to produce photoions 112 at tip 180 of sample 106. Photoions 112 propagating in ion trajectories 113 move in ion time-of-flight mass spectrometry direction 186 from sample 106 to ion detector 114.

Moreover, primary electrons 110 impinge upon tip 180 of sample 106 to produce scattered electrons 116 that arrive at electron detector 118 in electron diffraction pattern 184. Also, due to primary electrons 110 impinging upon 180 of sample 106, scattered electrons are detected by electron detector 122 as electron micrograph 182. It will be appreciated that production of photoions 112 occurs in a presence of EUV radiation 104 and in an absence of primary electrons 110. It further will be appreciated that production of scattered electrons (116, 122) occurs in a presence of primary electrons 110 and in an absence of EUV radiation 104 or in an absence of an electrical field between sample 106 and extraction electrode 150.

According to an embodiment, hybrid EUV imaging spectrometer 100 includes sample 106 disposed on stage 152 that is disposed in chamber 126. In a certain embodiment, pulsed EUV radiation 104 is from radiation source 102 enters chamber 126 through coupler 124. Pulsed EUV radiation 104 is directed and focused by EUV optics 128 disposed in chamber 126 and is incident upon sample 106. In a certain embodiment, stage 152 adjusts a position of sample 106 with respect to extraction electrode 150. A voltage difference (produced by a bias voltage applied to extraction electrode 150 or sample 106) between extraction electrode 150 and sample 106 provides an electric field therebetween to accelerate and to remove photoions 112 produced in response to EUV radiation 104 of tip 180 of sample 106. Photoions 112 traverse aperture 152 of extraction electrode 150 and impact ion detector 114, e.g., a two-dimensional position-sensitive.

In an embodiment, voltage difference between extraction electrode 150 and sample 106 is selectively adjustable to control a rate of impact of photoions 112 on ion detector 114. A position or focus of EUV radiation 104 incident on sample 106 is selectively adjustable to produce EUV radiation-assisted field evaporation of photoions 112 from sample 106. Sample 106 is irradiated by primary electrons 110 produced by electron source 108. Scattered electrons 116 transmitted or diffracted by sample 106 are detected by electron detector 118. Secondary or backscattered electrons 120 emitted from tip 180 of sample 106 are detected by electron detector 122. An interior of chamber 126 has a pressure that can be ultra-high-vacuum provided, e.g., by a vacuum pumping system. The vacuum pumping system can include a vacuum pump such as a titanium sublimation pump, cryogenic, helium refrigerator, diffusion pump, turbo molecular pump, and the like. Optical camera 130 monitors a position or condition of components disposed in chamber 126.

Hybrid EUV imaging spectrometer 100 includes radiation source 102 to produce EUV radiation 104 for photoionization of atoms of sample 106 to form photoions 112. In an embodiment, radiation source 102 can include a pulsed laser and a gas cell, wherein the gas cell receives a gas that is subjected to pulsed laser light from the pulsed laser to produce EUV radiation 104. Here, EUV radiation 104 can be produced as pulsed light by directing the pulsed laser light into the gas cell that includes a gas such as Kr, Xe, Ar, He, Ne, or a combination thereof. Without wishing to be bound by theory, it is believed that EUV radiation 104 is produced by high harmonic generation of the pulsed laser light by the gas in the gas cell. In an embodiment, pulsed EUV radiation 104 is provided by a high voltage electrical discharge of a gas in a capillary cell. In some embodiments, pulsed EUV radiation 104 is provided by synchrotron radiation. In a particular embodiment, pulsed EUV radiation 104 is produced by a free electron laser.

Figure 6:
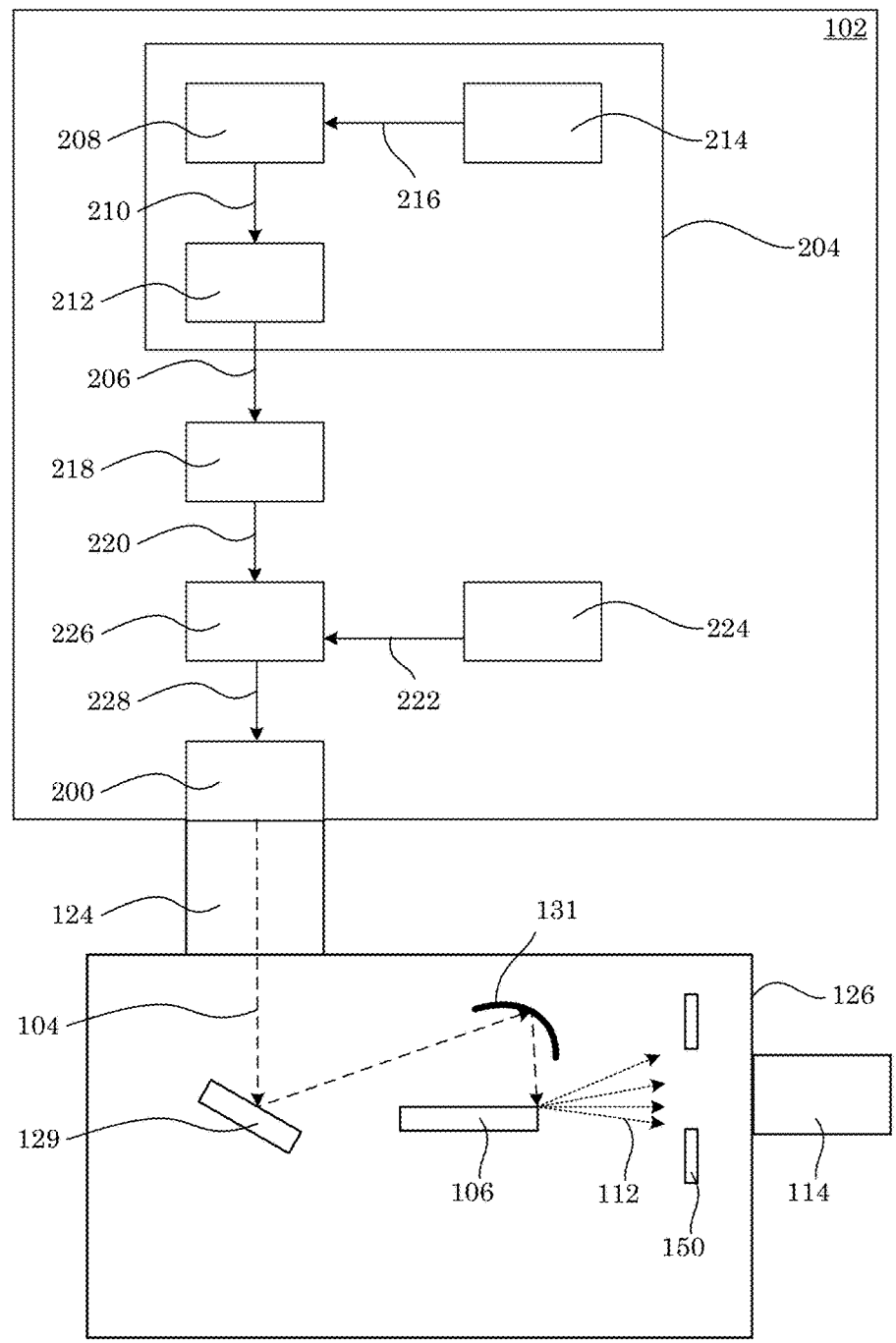
FIG. 6 shows a radiation source.

According to an embodiment, with reference to FIG. 6, radiation source 102 includes pump module 204 to produce pump light 206. Pump module 204 can include host laser 208 that produces host laser light 210 that is communicated from host laser 208 to frequency doubler 212. Pump module 204 receives diode light from laser diode 214, and frequency doubler 212 doubles host laser light 210 (i.e., doubles the energy or halves the wavelength via frequency doubling, e.g., in an optical crystal). Pump light 206 is received by mode-locked laser 218 from pump module 204, wherein mode-locked laser 218 produces laser output 220 that is received by amplifier 226. Amplifier 226 also receives amplifier light 222 from amplifier pump 224 to amplify laser output 220 into pulsed light 228. Pulsed light 228 is communicated from amplifier 226 to high harmonic generator 200. High harmonic generator 200 receives pulsed light 228 and produces EUV radiation 124, which is pulsed.

Here, laser diode 214 can be a laser diode array that produces diode light 216 with an output power and wavelength (e.g., 800 nanometer (nm) continuous wave (CW) radiation with a selected power sufficient to pump host laser 208. Host laser 208 can be, e.g., neodymium (Nd)-doped yttrium aluminum garnet (YAG) laser or other laser that produces host laser light 210 that is CW and has a wavelength at about 1000 nm, although a different laser would provide a different wavelength. Frequency doubler 212 can produce doubled pump light 206, e.g., having CW output and a wavelength of about 500 nm, depending on the wavelength of host laser light 210. Mode-locked laser 218 can be a passively mode-locked laser such as a titanium sapphire (Ti:sapphire) laser to produce laser output 220 having a wavelength, e.g., of about 800 nm with a repetition rate of about 80 MHz.

The resulting output of mode-locked laser 218 is communicated to amplifier 226, which can be a Ti:sapphire regenerative amplifier, to produce pulsed light 228 at a wavelength of about 800 nm at a selected frequency, e.g., about 10 kiloHertz (kHz) with a selected pulse energy, e.g., of about 0.5 milliJoules (mJ)/pulse. Pulsed light 228 can have a selected pulse width such as 35 femtoseconds (fs). EUV flux from high harmonic generator 200 can be, e.g., 45 eV photons emerging as EUV radiation 104 at a rate of $10^{12}$ photons/pulse with, e.g., 0.72 nJ/pulse. Exemplary high harmonic generation for various gases in high harmonic generator 200 to produce EUV radiation 104 are listed in Table 1.

TABLE 1

| Gas | EUV energy (electron volts (eV)) | Wavelength (nm) |
|---|---|---|
| Combination of krypton and xenon | 10-30 | 124-41 |
| Argon | 35-45 | 35-26 |
| Neon | 40-100 | 31-12 |
| Helium | 100 | 12 |

In an embodiment, coupler 124 receives pulsed EUV radiation 104 from high harmonic generator 200 of radiation source 102 and communicates pulsed EUV radiation 104 chamber 126. Here, an interior of coupler 124 has a pressure that is compatible with propagation of EUV radiation 104 from radiation source 102, e.g., a high harmonic generator 200, to chamber 126. An exemplary pressure of chamber 126 is ultrahigh vacuum. An optical interface between radiation source 102 and coupler 124 can be an EUV optical window (e.g., a metal foil such as an aluminum foil) to transmit EUV radiation 104 therethrough and to transmit EUV radiation 104 into chamber 126.

Disposed in chamber 126 is EUV optic 128 to receive EUV radiation 104 from coupler 124. EUV optics 128 can include mirror 129 and concave reflector 133. Mirror 129 can be a flat mirror, curved EUV mirror, and the like or a combination thereof with concave reflector 133 can have a selected position or angle to adjust EUV radiation 104 with respect to sample 106. It is contemplated that EUV optics 128 (e.g., mirror 129, concave reflector 133, and the like) can focus EUV radiation 104 onto sample 106. In an embodiment, EUV optic 128 is a zone plate to focus EUV radiation 104 on sample 106.

Radiation source 102 can operate at a selected wavelength from 12 nm to 124 nm. The EUV wavelength band provides nearly uniform optical absorption across atoms in sample 106 with absorption depth in sample 106, e.g., of 10 nm. The absorption depth is selectively tunable and can depend upon the wavelength of EUV radiation 104. Moreover, the wavelength of EUV radiation 104 provides efficient photoionization of atoms and photo-disassociation of complex ions. EUV radiation 104 substantially photoionizes elemental species of atoms at tip 180 of sample 106 (see, e.g., a micrograph of sample 106 shown in FIG. 7) and contributes to additional photoionization and disassociation of molecular complexes. As used herein, "EUV light" and "EUV radiation" are identical.

Unexpectedly, surprisingly, and without wishing to be bound by theory, it is believed that a photoionization pathway for field evaporation of ions of sample 106 occurs through photoionization in a presence of EUV radiation 104 and is significantly different than irradiation of sample 106 with a UV wavelength. In conventional use of UV radiation, e.g., in an atom probe microscope, a UV wavelength from 255 nm to 355 nm (corresponding to photon energy from 4.9 eV to 3.5 eV) is less than a photoionization threshold for inorganic solid materials such that substantial photoionization does not occur. In contrast, hybrid EUV imaging spectrometer 100 produces EUV radiation 104 with a selected wavelength, e.g., from 12 nm to 124 nm to provide an EUV photon energy, e.g., from 10 eV to 100 eV. In this EUV band, photoionization cross-sections are large, and EUV radiation 104 can singly photoionize or multiply ionize atoms in sample 106 that can include a material of technological interest. EUV radiation 104 can have a substantially uniform optical absorption depth in sample 106, e.g., 10 nm in sample 106, e.g., a metal, plastic, ceramic, polymer, glass, semiconductor, insulator, conductor, hybrid materials composed of such constituents, and the like.

Further, conventional laser atom probes involve thermally-assisted field ion evaporation, wherein field ion evaporation provides removal of atoms from a sample by applying a high electric field (e.g., 10 volts (V)/nm to 60 V/nm) in a presence of UV light that impinges on a sample. In contrast hybrid EUV imaging spectrometer 100 includes EUV radiation 104 that photoionizes atoms of sample 106. Instead, hybrid EUV imaging spectrometer 100 uses EUV radiation 104 to provide photoionization-assisted field ion evaporation to produce photoions 112 from sample 106 that are produced by electronic excitation. That is, with UV radiation (e.g., 255 nm to 355 nm UV light), thermal pulsing dominates, and significant photoionization does not occur. EUV radiation 104 provides photoionization of constituent atoms of sample 106.

Although photoionization cross-sections can vary among elements of the periodic table, hybrid EUV imaging spectrometer 100 with EUV radiation 104 reduces an element-to-element variation in production of photoions 112 compared to conventional atom probe tomography, which employs UV lasers. Element-to-element differences in the field evaporation rate for a conventional pulsed-laser atom probe, in which absorbed pulsed laser light imparts transient increases in temperature of the specimen tip and involves a difference in a zero-barrier evaporation field F. Unexpectedly and surprisingly, element-to-element differences in the evaporation rate in hybrid EUV imaging spectrometer 100 with pulsed EUV radiation 104 are due to differences in photoionization cross-section because surface species that have been photoionized will generally experience reduced bonding strength to the specimen tip. In thermally assisted pulsing with UV light, the evaporation rate is exponentially dependent on both F and temperature such that changes in applied field F lead to changes in evaporation rate with higher temperature thermal transients yielding greater evaporation rates. Therefore, materials or portions of samples that have relatively reduced UV absorption will yield relatively reduced evaporation rates. For pulsed EUV radiation 104, the contribution to the evaporation rate that is dependent on photoionization is unexpectedly and surprisingly linearly dependent on absorption cross-section σ such that element-to-element differences in σ have less influence on the evaporation rate. Additionally, the EUV absorption depth d is unexpectedly and surprisingly comparable or smaller than typical specimen tip diameters for a wide variety of materials of interest, e.g. for 45 eV photons: d=200 nm for Si; d=35 nm for GaAs; d=15 nm for GaN; d=20 nm for Fe; d=35 nm for SiN; d=20 nm for $SiO_2$; d=12 nm for $Al_2O_3$; d=4 nm for $TiO_2$—and so on. Therefore, the thermally-assisted pathway for field evaporation provided by pulsed EUV will generally be far more uniform compared to what is attainable with pulsed UV. Moreover, EUV radiation 104 produces substantially fewer complex ions than UV light, wherein a sample subjected to UV light can produce molecular ions due to thermally-assisted process such as surface diffusion on the sample. EUV radiation 104 provides photoionization and photodissociation of complex ions formed from subjecting sample 106 to EUV radiation 104. As a result, formation of neutral species or complex ions such as molecular ions from sample 106 are substantially absent in a presence of EUV radiation 104 received by sample 106.

Sample 106 is subjected to EUV radiation 104 and primary electrons 110. Photoions 112 are produced from photoionization of atoms of sample 106. Scattered electrons 116 and scattered electrons 120 produced by transmission, diffraction, secondary mission, and the like of electrons in response to subjecting sample 106 to primary electrons 110. Sample 106 can include any material subject to photoionization by EUV radiation 104. Exemplary materials include polymers, glasses, other covalently bonded materials, and the like. Sample 106 can have any shape, e.g., a conical shape, spherical, planar, and the like.

Figure 7:
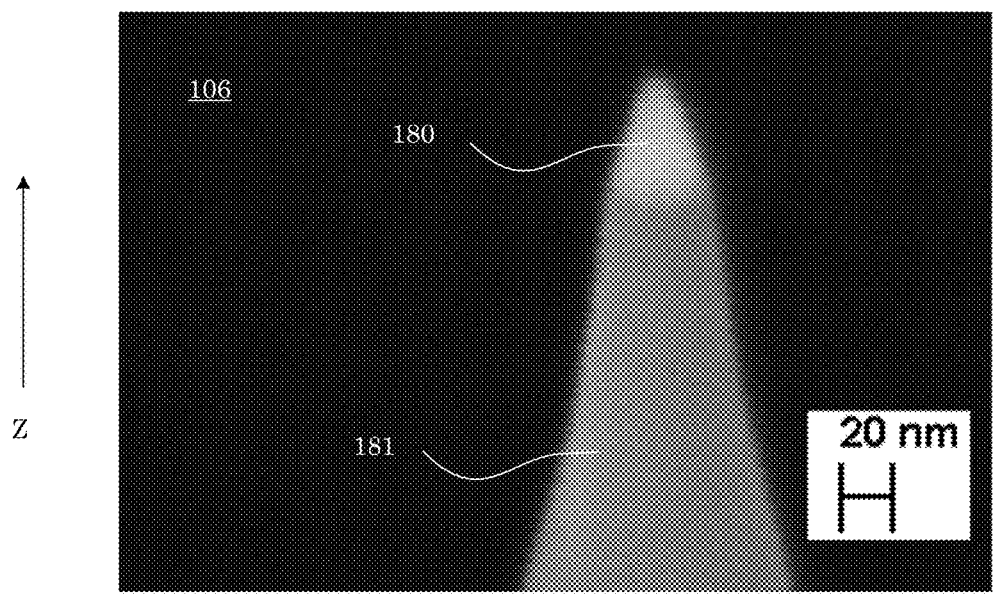
FIG. 7 shows an electron micrograph of a sample.
Figure 8:
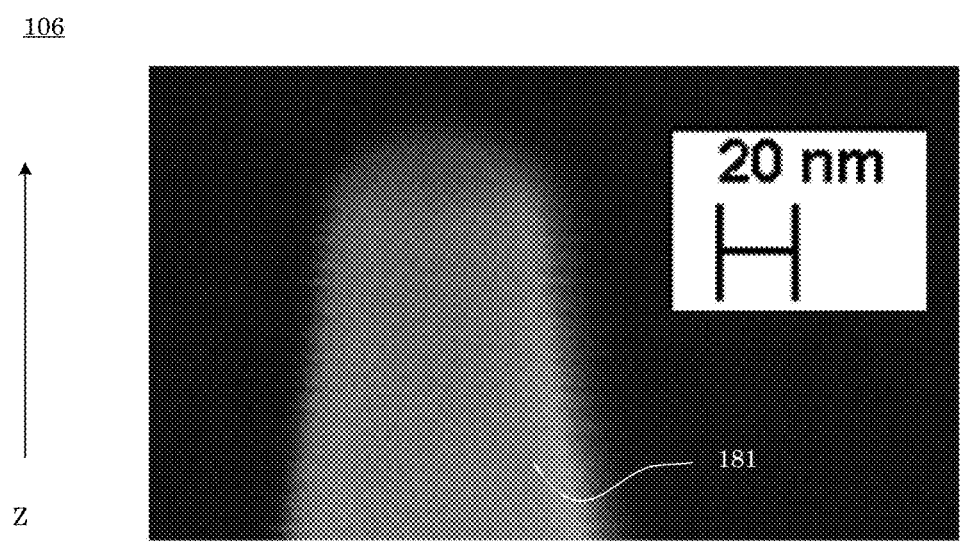
FIG. 8 shows an electron micrograph of the sample shown in FIG. 7 after the sample was subjected to pulsed EUV radiation in a presence of an external electric field.

In an embodiment, with reference to FIG. 7, sample 106 include tip 180 and body 181. As atoms of tip 100 are removed by photoionization under irradiation by EUV radiation 104 in a presence of an external field present between sample 106 and extraction electrode 150, constituent atoms comprising tip 180 are removed from body 181 as shown in FIG. 8. It is contemplated that a composition of sample 106 can change in tip 180 or body 181. According to an embodiment, sample 106 is prepared by annular milling in the focused ion beam microscope, and sample 106 has axial symmetry. The axial symmetry of tip 180 can be confirmed by of electron tomography.

Stage 152 can provide control of a position of sample 106 in chamber 126, in particular with relation to extraction electrode 150. Further, stage 152 can control a temperature of sample 106, remove sample 106 from chamber 126, insert sample 106 into chamber 126 without substantially changing the vacuum level (e.g., the ultrahigh vacuum) of chamber 126, or a combination thereof. Chamber 126 can include additional components such as a load-lock chamber, transfer arm, and the like to manipulate (e.g., move or dispose) extraction electrode 150, sample 106, and the like in chamber 126.

Figure 9:
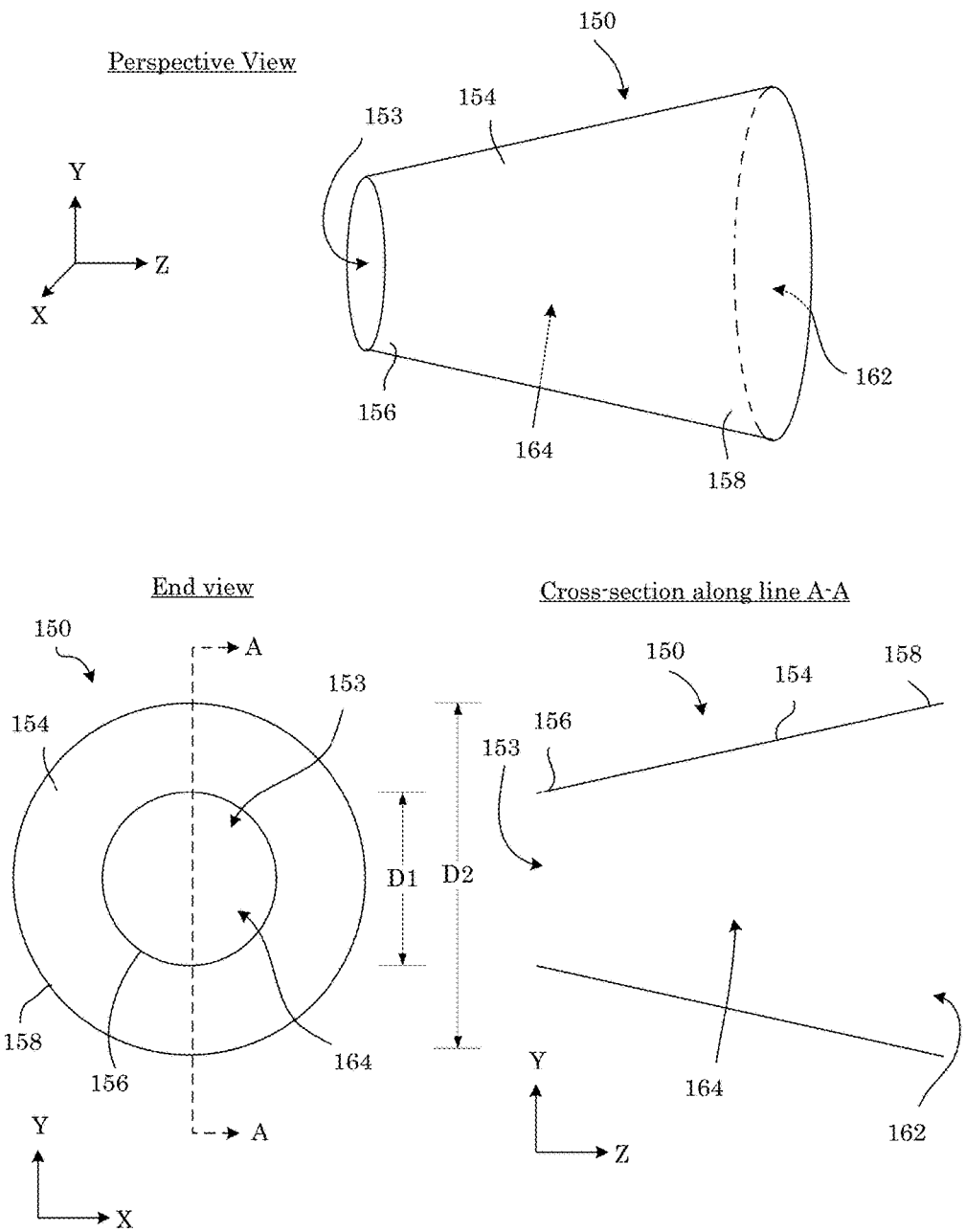
FIG. 9 shows an extraction electrode in perspective view, an end view, and a cross-sectional view.

Ion optics, e.g., extraction electrode 150, are disposed proximate to sample 106 and interposed between sample 106 and ion detector 114. In an embodiment, with reference to FIG. 9 (perspective view, in view, and cross-section along line A-A), ion optics includes extraction electrode 150. Ion optic 150 includes first end 156 disposed proximate to sample 106 and distal to ion detector 114, second end 158 disposed proximate to ion detector 114 and distal to sample 106, entry aperture 153 through which photoions 112 are transmitted and traverse extraction electrode 150 in electrode interior 164 bounded by wall 154 and exit extraction electrode 150 at exit aperture 152. In an embodiment, the ion optics can include a reflectron disposed to receive photoions 112 transmitted by extraction electrode 150 from sample 106 and to communicate photoions to ion detector by reflecting the photoions in a presence of an electric field in the reflectron.

Figure 10:
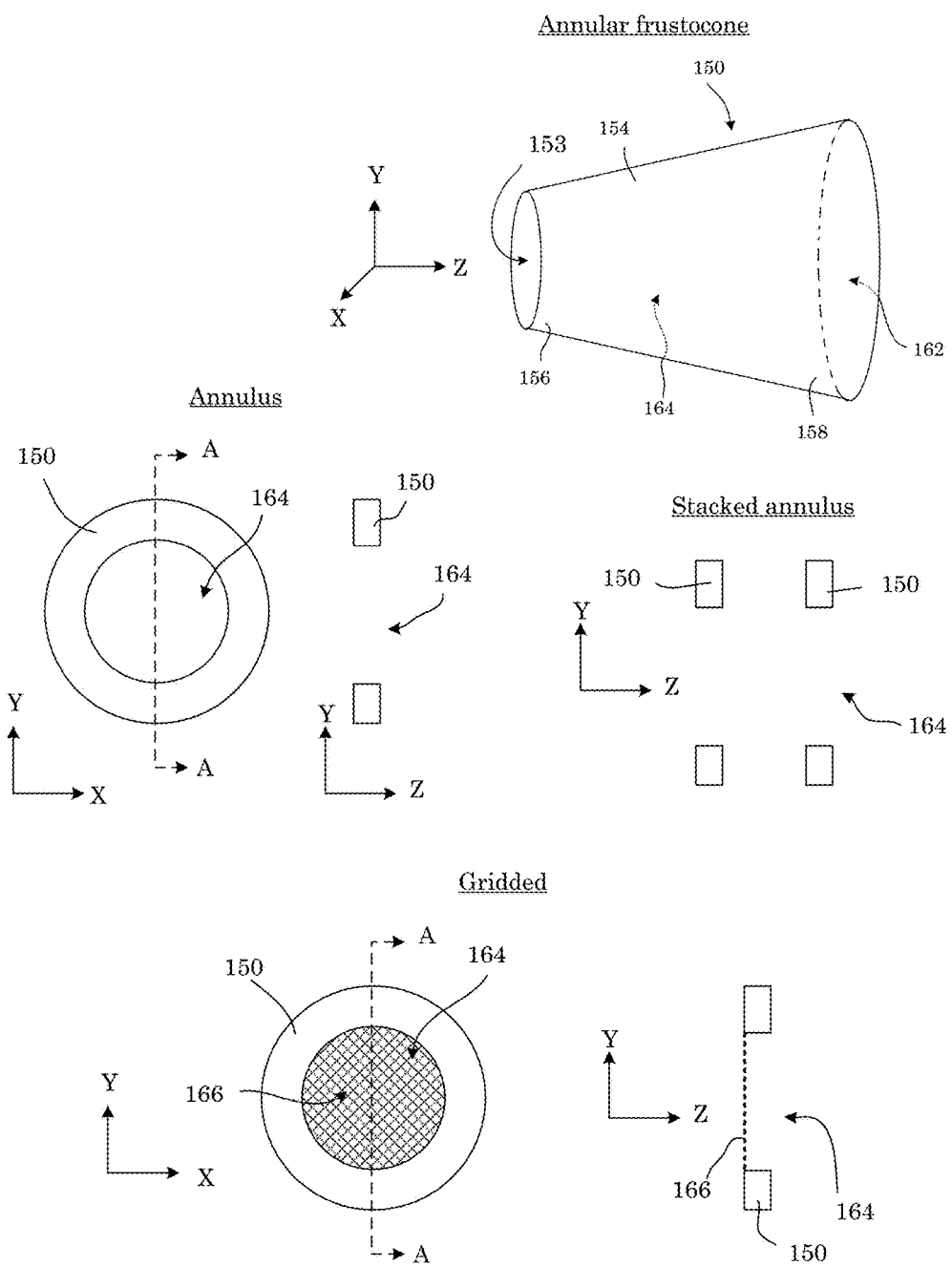
FIG. 10 shows a plurality of extraction electrodes.

A size and shape of the of extraction electrode and ion optics 150 can be selected to communicate photoions 112 from sample 106 two ion detector 114. As shown in FIG. 10, extraction electrode 150 can be an annular first cone, annulus, stacked annulus, gridded and the like. The annular first to cone form of extraction electrode 150 is shown in both FIG. 9 and FIG. 10. Moreover, as indicated by stacked annulus extraction electrode 150 in FIG. 10, a plurality of extraction electrodes 150 can be used in tandem and spaced apart spatially to provide focusing or a selected electric field profile to photoions 112. In gridded extraction electrode 150, electrically insulating grid 166 is disposed to cover the entry aperture but provide communication of photoions 112 through extraction electrode 150.

In an embodiment, extraction electrode 150 receives a bias voltage such that a potential difference exists between extraction electrode 150 in sample 106. Aperture 153 of extraction electrode 150 communicates photoions 112 emitted from sample 106 to ion detector 114. Extraction electrode 150 can be disposed in or removed from chamber 126 without substantially changing the ultra-high vacuum of chamber 126. Hybrid EUV imaging spectrometer 100 that includes extraction electrode 150 in combination with sample 106 and ion detector 114 provides acquisition of mass-spectral data and reliable chemical assignments with spatial resolution for mapping materials of sample 106.

Ion detector 114 receives photoions 112 emitted from sample 106. Here, ion detector 114 records arrival of photoions 114, a time taken by photoions 112 to traverse a distance between sample 106 and ion detector 114, a position of arrival on ion detector 114, or a combination thereof. Exemplary ion detectors 114 is a microchannel plate, an electron multiplier modified to detect cations, a Faraday cup, and the like. Exemplary ion detectors also include a those that can record kinetic energy of detected ions and permit determination of the mass of a detected ion. In an embodiment, ion detector 114 is a two-dimensional position-sensitive detector disposed in chamber 126 to detect or record photoions 112 emitted from sample 106 as a function of time-of-arrival based at ion detector 114 and as a function of a position on ion detector 114. Ion detector 114 can include ion optics disposed prior to a detecting surface to steer, focus, pulse, mass select, velocity image, and the like photoions 112. In this manner, ion detector 114 performs time-of-flight mass spectrometry and ion imaging of photoions 112 released from sample 106 in response to sample 106 subjected to EUV radiation 104 that photoionizes atoms of sample 106. From the time of arrival of photoions 112 at ion detector 114 from sample 106, a mass of each photoion 112 can be determine based on the potential difference (i.e., electric field strength) present between sample 106 and extraction electrode 150 when photoions 112 are created. EUV radiation 104 singly photoionizes atoms of sample 106 to produce singly charged photoions 112, and the masses determined from the time-of-flight mass spectrum acquired by ion detector 114 identify the element (i.e., atom) in sample 106 that produced photoions 112. Multiply charged photoions may yield ambiguous assignments since purely time-of-flight detection schemes are sensitive to the ratio on ionic mass divided by ionic charge—hence, multiply charged heavier species may be indistinguishable from singly charged lighter ones. This ambiguity can be eliminated if the detection scheme records both the ionic time-of-flight and the kinetic energy of the detected ion. In such a scheme, the ionic mass can be unequivocally determined. From the position of photoions 112 incident at ion detector 114, a position on sample 106 of the atoms that produced photoions 112 can be determined. The mass of the photoions and the position of the atoms on sample 106 are used in part to determine an elemental composition of sample 106 as a function of position on sample 106. Electron imaging described below in combination with the mass of the photoions in the position of the atoms in sample 106 provide three-dimensional chemical maps of sample 106.

In an embodiment, electron source 108 is in communication with and coupled to chamber 126 to provide primary electrons 110, e.g., an electron beam, to chamber 126, wherein primary electrons 110 impinge upon sample 106. Electron source 108 includes an electron emitter and electron optics. The electron emitter emits electrons that can be subjected to collimation, focusing, energy control (e.g., acceleration, selection, and the like) by the electron optics. Exemplary electron emitters include a field emitter, thermionic emitter, and the like. Primary electrons 110 can have a selected energy, flux, spot size of sample 106 effective to produce scattered electrons (116, 120). The acceleration voltage of primary electrons 110 can be from 0 to 30 kV, e.g., 25 kV. The beam current of primary electrons 110 can be from 5.2 pA to 7.2 nA, with beam current that is, e.g., 20 pA. The spot diameter of primary electrons 110 at sample 106 can be from 4 nm to 100 nm and a typical operational spot diameter is 4 nm. Primary electrons 110 can have a static position at sample 106 or can be scanned (e.g., rastered) over sample 106.

Sample 106 is subjected to primary electrons 110. In response to primary electrons 110, scattered electrons (116, 120) are produced. Scattered electrons 116 are received by electron detector 118. Electron detector 118 can include a transmission electron imaging detector or an electron diffraction detector. Scattered electrons 120 are received by electron detector 122. Electron detector 122 can be a secondary emission electron detector or an electron backscatter detector. In this manner, in-situ electron imaging of sample 106 is provided by electron source 108, electron detector 118, and electron detector 122 in chamber 126 of hybrid EUV imaging spectrometer 100. As a result, hybrid EUV imaging spectrometer 100 provides near-real-time measurement of a time-varying shape of tip 180 of sample 106 during data acquisition in an absence of dismounting sample 106 or interrupting data acquisition or changing a state of the vacuum in chamber 126. Accordingly, hybrid EUV imaging spectrometer 100 provides scanning electron microscopy (SEM) and scanning transmission electron microscope (STEM) modes as well as capturing transmission electron diffraction patterns with sample 106 disposed proximate to extraction electrode 150. Electron imaging and detection with electron detector (118, 122) can occurs in combination with production of photoions 112 from EUV radiation 104 in combination with the external electric field applied between sample 106 and extraction electrode 150, e.g., by alternating impingement of primary electrons 110 on sample 106 with detection of scattered electrons (116, 120) by electron detector (118, 122) and impingement of EUV radiation 104 on sample 106 with detection of photoions 112 by ion detector 114 and external electric field applied between sample 106 and extraction electrode 150.

In an embodiment, electron detector 118 is disposed on chamber 126 to detect diffraction or imaging of primary electrons 110 impinging on sample 106 from electron source 108 as scattered electrons 116.

In an embodiment, electron detector 122 is disposed on chamber 126 to detect secondary or backscattered electrons emitted by sample 106 as scattered electrons 120 due to primary electrons 110 originating from electron source 108 and impinging on sample 106.

Additionally, hybrid EUV imaging spectrometer 100 includes in-situ real-time electron imaging of scattered electrons (116, 120) to record the shape of tip 180 of sample 106 and uses that information in a reconstruction algorithm to determine the shape and composition of sample 106 as a function of time and space.

Electron imaging (e.g., scanning transmission, secondary electron and diffraction) by electron detector (118, 122) to measure the shape of sample 106 at intermediate stages in the data collection process provides the direct, in-situ electron beam imaging of sample 106 to eliminate interpolation of the shape of tip 180 of sample 106 between before and after only images or for ex-situ electron imaging. Beneficially and unexpectedly, hybrid EUV imaging spectrometer 100 provides computational accuracy of three-dimensional (3-D) reconstruction of the shape and composition of sample 106.

Figure 11:
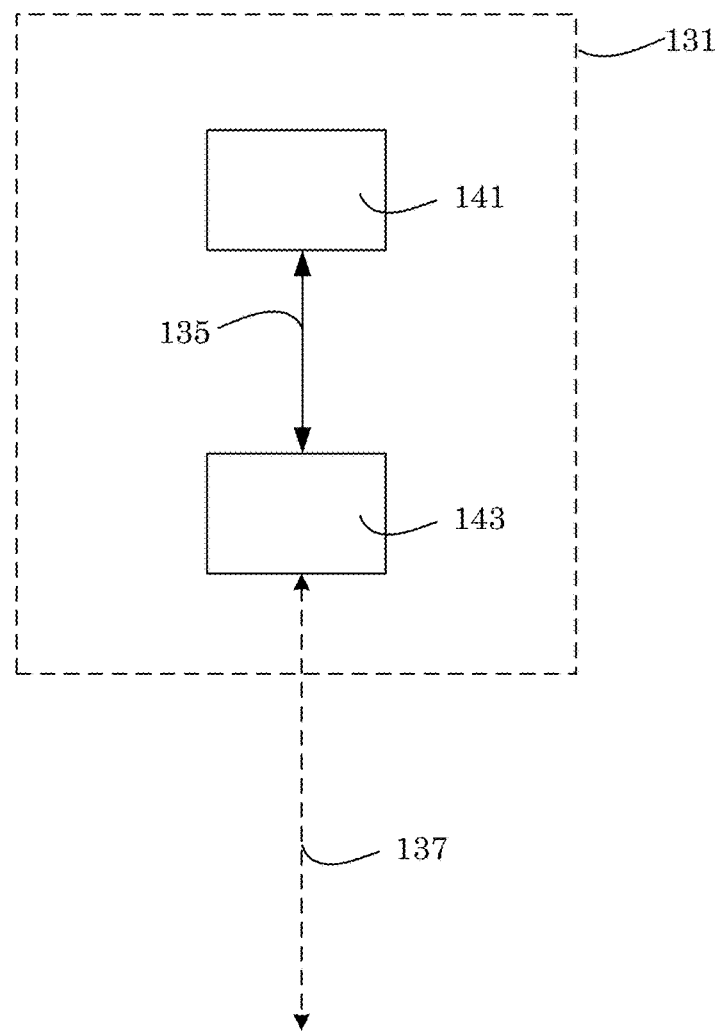
FIG. 11 shows an analyzer.

Electron data 134 acquired by electron detector 118, electron data 138 acquired by electron detector 122, and ion data 136 acquired by ion detector 114 are communicated to analyzer 131. With reference to FIG. 11, analyzer 131 can include control module 143 and data analysis module 141 interconnected and in electrical communication by data path 135. Control module 143 communicates, controls, monitors, or records functions of and data acquired (e.g., EUV source data 132, electron data 134, electron data 138, electron source data 140, ion data 136, sample data 160, extraction electrode data 161, pressure of chamber 126, and the like) by chamber 126, EUV source 102, in-chamber inspection camera 130, electron source 108, electron detector 118, electron detector 122, ion detector 114 using data path 137.

Data accumulated in control module 143 from sample 106 includes position-sensitive time-of-flight mass spectral information (e.g., ion data 136) and specimen shape information. These data along with other data are communicated to data analysis module 141 in data path 135. Data analysis module 141 analyzes this combined data to determine three-dimensional chemical maps of sample 106. Control module 143 can include hardware (e.g., a microprocessor and the like), software (e.g., an algorithm, script, or other code) to make the determination of the three-dimensional chemical maps of sample 106.

In an embodiment, a process for making hybrid EUV imaging spectrometer 100 includes disposing electron source 108 on chamber 126 to emit primary electrons 110 into chamber 126 to subject sample 106 to primary electrons 110; disposing electron detector 118 on chamber 126 to detect electron diffraction or to perform electron imaging of scattered electrons 116 from sample 106 in response to subjecting sample 106 to primary electrons 110 from electron source 108; disposing electron detector 122 on chamber 126 to detect secondary electrons or backscattered electrons as scattered electrons 120 emitted from sample 106 in response to subjecting sample 106 to primary electrons 110 from electron source 108; disposing radiation source 102, coupler 124, and EUV optics 150 on chamber 126 to provide pulsed EUV radiation 104 into chamber 126, to steer and focus EUV radiation 104, and to subject sample 106 to EUV radiation 104; disposing stage 152 in chamber 126 to receive sample 106; disposing extraction electrode 150 and ion detector 114 on chamber 126 such that photoions 114 produced by sample 106 in response to being subjected to EUV radiation 104 and the electric field between sample 106 and extraction electrode 150 are communicated through extraction electrode 150 to ion detector 114 from sample 106 and impact ion detector 114 and a presence a voltage difference between sample 106 and extraction electrode 150.

According to an embodiment, a process for performing hybrid EUV imaging spectrometry of sample 106 includes producing, by radiation source 102, EUV radiation 104; subjecting sample 106 to EUV radiation 104; photoionizing a plurality of atoms of sample 104 with EUV radiation 104; forming photoions 112 from the atoms subject to single photoionization by EUV radiation 104; field evaporating photoions 112 from sample 106 in response to sample 106 being subjected to EUV radiation 104 and an electric field between sample 106 and extraction electrode 150; detecting, by ion detector 114, photoions 112: as a function of a time-of-arrival of photoions 112 at ion detector 114 after sample 106 is subjected to EUV radiation 104, or as a function of a position of photoions 112 at ion detector 114; producing, by electron source 108, a plurality of primary electrons 110; subjecting sample 106 to primary electrons 110; forming scattered electrons from sample 106 in response to sample 106 being subjected to primary electrons 110; detecting, by the electron detector, the scattered electrons: as a function of a time-of-arrival of the scattered electrons at the electron detector after sample 106 is subjected to EUV radiation 104 or primary electrons 110, or as a function of a position of the scattered electrons at the electron detector; and acquiring, by analyzer 131, data from ion detector 114 and the electron detector to image sample 106. The process can include reconstructing a shape of sample 106; and determining a chemical composition of sample 106 as a function of position in sample 106. The process can include determining a tomographic shape and composition of sample 106. The process can include transmitting, by extraction electrode 150, photoions 112 from sample 106 to ion detector 114, wherein extraction electrode 115 includes aperture 153 to transmit photoions 112, and extraction electrode 150 is disposed proximate to sample 106 and interposed between sample 106 and ion detector 114.

The process also can include applying a potential difference between sample 106 and extraction electrode 150; decreasing the potential difference to detect the scattered electrons; and increasing the potential difference to detect photoions 112. Sample 106 can be subjected to EUV radiation 104 after the potential difference is increased to form photoions 112; and detecting, by ion detector 114, photoions 112 includes performing time-of-flight mass spectrometry on photoions 112.

According to an embodiment, a process for performing hybrid EUV imaging spectrometry on sample 106 includes disposing sample 106 on stage 152; disposed stage 152 and sample 106 in chamber 126; applying a voltage bias between sample 106 and extraction electrode 150; subjecting sample 106 two pulsed EUV radiation 104; optionally monitoring and recording pulsed EUV radiation 104 incident on sample 106; producing photoions 112 in response to subjecting sample 106 to the EUV radiation 104; receiving photoions 112 at ion detector 114; recording a time-of-flight of photoions 112 between sample 106 and ion detector 114 by control module 143; recording the positions upon ion detector 114 at which photoions 112 impact ion detector 114 by control module 143; providing electronic feedback control to control the voltage bias between sample 106 and extraction electrode 150; optionally adjusting the voltage bias to obtain a selected rate of impact of photoions 112 on ion detector 114; optionally providing electronic feedback control to control a selected position or focus of pulsed EUV radiation 104 upon sample 106; adjusting the bias voltage between sample 106 and extraction electrode 150 zero volts (V) at a selected period during data acquisition while EUV radiation 104 is substantially absent at sample 106, wherein during the period, subjecting sample 106 to primary electrons 110 and detecting scattered electrons by detector 118 to acquire transmission electron diffraction or electron imaging of sample 106; optionally detecting, by electron detector 122, secondary electrons or backscattered electrons from sample 106 during the interval when the voltage bias is zero V and primary electrons 110 impinge upon sample 106; terminating the first interval and terminating subjecting sample 106 to primary electrons 110; during a second interval, increasing the voltage bias between sample 106 and extraction electrode 150, subjecting sample 106 to EUV radiation 104, and acquiring time-of-flight mass spectra of photoions 112 and positions of impact of photoions 112 on ion detector 114 to perform hybrid EUV imaging spectrometry on sample 106. The alternating cycle between the first interval and the second interval, wherein EUV radiation-assisted ionic field evaporation of photoions 112 is alternated with electron-sample interactions and scattered electron detection, can be performed a plurality of times. During data acquisition, ion time-of-flight data, ion impact positions on ion detector 114, diffraction data, electron imaging data, secondary electron data, and electron backscattered data collected from sample 106 by electron source 108 and detectors (114, 118, 122) as well as data associated with other components of hybrid EUV imaging spectrometer 100 are acquired by control module 143 or communicated to data analysis module 141 to reconstruct shape and composition of sample 106.

Figure 12:
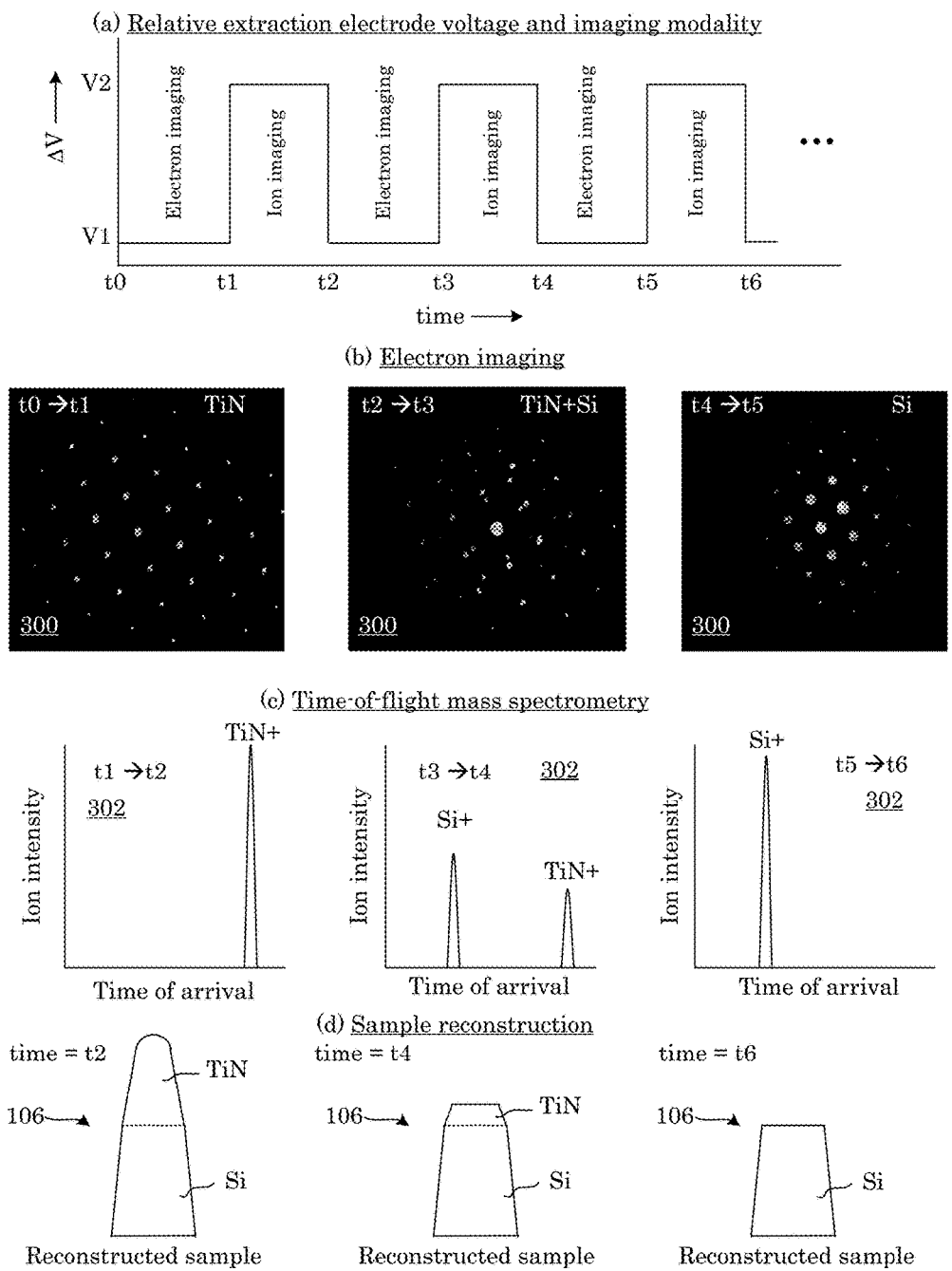
FIG. 12 shows (panel A) a graph of voltage versus time, (panel B) electron diffraction images, (panel C) ion time-of-flight (TOF) mass spectra of photoions, and (panel D) reconstruction of a sample.

With reference to FIG. 12, panel A of FIG. 12 shows a graph of the potential difference ΔV between sample 106 and extraction electrode 150 versus time.

Between time t0 and time t1, potential difference ΔV is first voltage V1 such that an imaging modality of hybrid EUV imaging spectrometer 100 is electron imaging, wherein primary electrons 110 impinge upon sample 106 and electron imaging and detection by electron detectors (118, 122) occurs to acquire, e.g., electron diffraction images as shown in panel B of FIG. 12. As shown in panel A of FIG. 12, between time t1 and time t2, potential difference ΔV is second voltage V2 such that an imaging modality of hybrid EUV imaging spectrometer 100 is ion imaging and the time-time-of-flight mass spectrometry acquisition occurs, wherein EUV radiation 104 impinges upon sample 106, and ion imaging and detection by ion detector 114 occurs to acquire, e.g., time-of-flight mass spectrometry of photoions 112 emitted from sample 106 as shown in panel C of FIG. 12. At time t2, analyzer 131 reconstructs the geometrical shape and chemical composition of sample 106 from electron data and ion data as shown in panel D of FIG. 12.

As shown in panel A of FIG. 12, between time t2 and time t3, potential difference ΔV is first voltage V1 such that an imaging modality of hybrid EUV imaging spectrometer 100 is electron imaging, wherein primary electrons 110 impinge upon sample 106 and electron imaging and detection by electron detectors (118, 122) occurs to acquire, e.g., electron diffraction images as shown in panel B of FIG. 12. As shown in panel A of FIG. 12, between time t3 and time t4, potential difference ΔV is second voltage V2 such that an imaging modality of hybrid EUV imaging spectrometer 100 is ion imaging in which the time-of-flight mass spectrometry acquisition occurs, wherein EUV radiation 104 impinges upon sample 106, and ion imaging and detection by ion detector 114 occurs to acquire, e.g., time-of-flight mass spectrometry of photoions 112 emitted from sample 106 as shown in panel C of FIG. 12. At time t4, analyzer 131 reconstructs the geometrical shape and chemical composition of sample 106 from electron data and ion data.

As shown in panel A of FIG. 12, between time t4 and time t5, potential difference ΔV is first voltage V1 such that an imaging modality of hybrid EUV imaging spectrometer 100 is electron imaging, wherein primary electrons 110 impinge upon sample 106 and electron imaging and detection by electron detectors (118, 122) occurs to acquire, e.g., electron diffraction images as shown in panel B of FIG. 12. As shown in panel A of FIG. 12, between time t5 and time t6, potential difference ΔV is second voltage V2 such that an imaging modality of hybrid EUV imaging spectrometer 100 is ion imaging in the fight mass spectrometry acquisition occurs, wherein EUV radiation 104 impinges upon sample 106, and ion imaging and detection by ion detector 114 occurs to acquire, e.g., time-of-flight mass spectrometry of photoions 112 emitted from sample 106 as shown in panel C of FIG. 12. At time t6, analyzer 131 reconstructs the geometrical shape and chemical composition of sample 106 from electron data and ion data. Although only three cycles of electron imaging, ion imaging, and sample reconstruction are shown in FIG. 12, it should be appreciated that such cycles can be repeated as selected, interrupted, restarted, and the like. Moreover, it is contemplated that sample 106 can be subjected to structural or compositional modification during a cycle or after cycle such that such structural or compositional modification can be ascertained due to electron imaging, ion imaging, or sample reconstruction by hybrid EUV imaging spectrometer 100.

In an embodiment, data stored in control module 143 during data acquisition are communicated to data analysis module 141 via data path 135. Data analysis module 141 performs computations to generate three-dimensional chemical maps of sample 106. In performing these computations, data analysis module 141 employs data that includes the shape of sample 106 that is generated using electron source 108, electron detector 118, and electron detector 122; ion times-of-flight between sample 106 and ion detector 114; and photoions 112 impact positions on ion detector 114; and the voltage bias between sample 106 and extraction electrode 150.

According to an embodiment, a process for reconstructing the shape and composition of sample 106 includes: during a time interval within which a voltage is applied between sample 106 and extraction electrode 150, subjecting sample 106 to pulsed EUV radiation 104 such that photoions emitted by sample 106 impact positions on detector 114; recording times-of-flight of photoions 112; recording the detection sequence of photoions 112 on detector 114; and recording the impact locations of photoions 112 on detector 114. In this manner, a dataset is produced that includes a sequential record of photoions 114 that are identified by their respective times-of-flight. Furthermore, the dataset also includes a record of the positions on the specimen tip of sample 106 from which photoions 112 are emitted as computed using back-projection from respective impact locations on detector 114. At the end of this time interval, when the voltage between sample 106 and extraction electrode 150 is zero, a shape of sample 106 (e.g., tip 181) is recorded using electron source 108 and electron detector (118 or 122). A depth of sample 106 at which photoions 112 resided in sample 106 with respect to an initial position of a terminus of tip 181, i.e. before photoions 112 are removed, is determined by starting with the first detected photoion 112 as follow: assigning an equivalent volume to identified photoion 112, wherein the depth increment contributed by this equivalent volume corresponds to the thickness of a thin portion of tip 181 within a field of view of the detector and whose shape and surface area is measured by electron source 108 and detector combinations previously described. Further, in the process, the depth increment is initially assigned as a depth coordinate of the first photoion 112. Then this depth coordinate is corrected by measuring the shape of tip 181 and determining the additional depth increment that must be added given the location on the surface of sample 106 from which photoion 112 was emitted. The process proceeds for successive photoions in a similar fashion eventually identifying the elemental species and original location of each detected photoion from the specimen tip.

The near-real-time measurement of the shape of tip 180 of sample 160 via in-situ electron imaging by hybrid EUV imaging spectrometer 100 provides reconstruction analysis that includes providing dimensional information to analysis algorithms in conjunction with spatial or temporal data from the position-sensitive detectors (e.g., 118, 122, or 114). As used herein, "three-dimensional chemical maps," "reconstruction analysis," and "spatial reconstruction" are identical. Accordingly, data acquisition and analysis can be continuous and performed in an absence of terminating acquisition of data, removing sample 106 from chamber 126, or in other disruption. Beneficially, hybrid EUV imaging spectrometer 100 provides accurate calibration for three-dimensional spatial reconstruction of sample 106. Without wishing to be bound by theory, it is believed that for tip 180 with axial symmetry, a two-dimensional image of tip 180 is sufficient for determination of the chemical image map of sample 106. In an embodiment, axial symmetry of tip 180 is provided during application, e.g. by annular milling in a focused ion beam microscope. As a result, geometry parameters of tip 180 for an accurate three-dimensional spatial reconstruction is provided from two-dimensional electron image.

Figure 13:
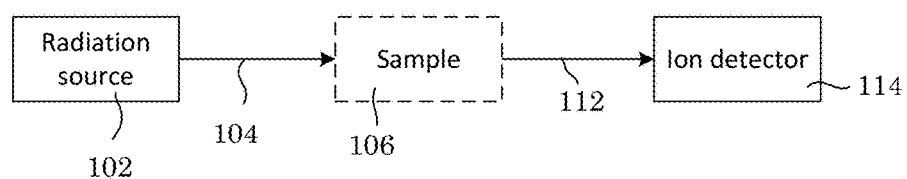
FIG. 13 shows an imaging spectrometer.

In an embodiment, with reference to FIG. 13, imaging spectrometer 100 includes radiation source 102 to produce EUV radiation 104 and is configured to subject sample 106 to pulsed EUV radiation 104, to photoionize a plurality of atoms of sample 106, and to form photoions 112 from the atoms subject to single photoionization by EUV radiation 104. Photoions 112 are radioactively field evaporated from sample 106 in response to sample 106 being subjected to EUV radiation 104. Also, imaging spectrometer 100 includes ion detector 114 to detect photoions 112 as a function of a time-of-arrival of photoions 112 at ion detector 114 after sample 106 is subjected to EUV radiation 104, or as a function of a position of photoions 112 at ion detector 114.

Figure 14:
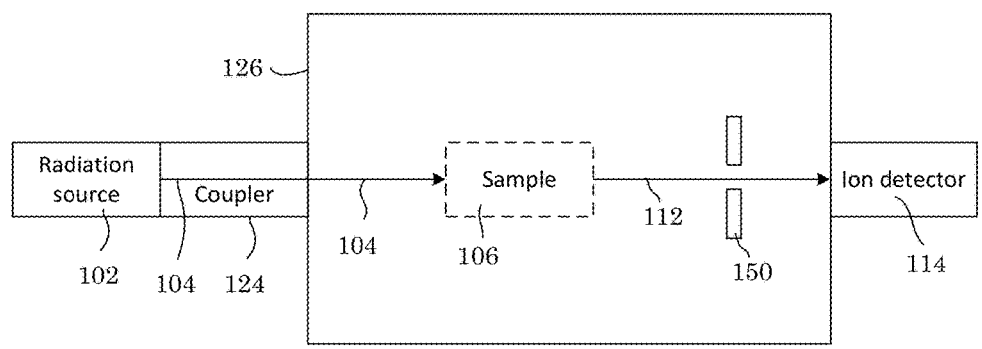
FIG. 14 shows an imaging spectrometer.

In an embodiment, with reference to FIG. 14, imaging spectrometer 100 includes chamber 126 (e.g., a vacuum chamber) in which is disposed sample 106. Ion optics 150 (e.g., an ion extraction electrode) can be interposed between radiation source 102 and ion detector 114, specifically interposed between sample 106 and ion detector 114 to extract photoions 112 released from sample 106 and to communicate photoions 112 to ion detector 114. According to an embodiment, extraction electrode 150 is disposed proximate to sample 106 and interposed between sample 106 and ion detector 114, wherein extraction electrode 150 includes an aperture to transmit photoions 112 from sample 106 to ion detector 114.

Coupler 124 is interposed between radiation source 102 and chamber 126 to optically couple radiation source 102 to sample 106 disposed in chamber 126. In this manner, EUV radiation 104 can be produced and transmitted without negatively impacting affluence of EUV radiation 104 such as by absorption of atmospheric gases before EUV radiation 104 interacts with sample 106. Here, chamber 126 provides a platform to dispose and arrange sample 106 relative to radiation source 102, electron source 108, and detectors 114, 118, 122. Further, chamber 126 provides a selected environmental condition for sample 106, EUV radiation 104, and photoions 112. The selected environmental condition can include temperature, pressure, gas composition, ultra-high vacuum, and the like.

Figure 15:
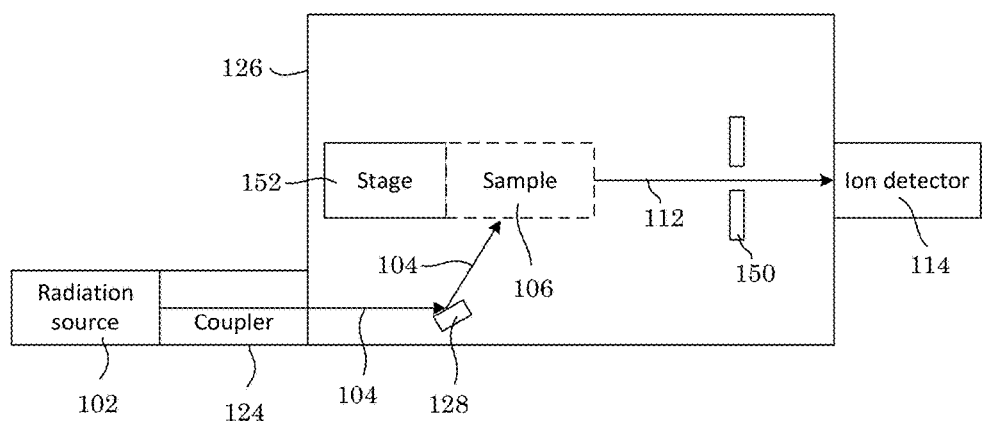
FIG. 15 shows an imaging spectrometer.

In an embodiment, with reference to FIG. 15, imaging spectrometer 100 includes EUV optic 128 disposed in chamber 126 to communicate and to selectively direct EUV radiation 104 from a radiation source 102 to sample 106. Stage 152 disposed in chamber 126 receives sample 106, wherein sample 106 can be mounted on stage 152. A position of sample 106 relative to components (e.g., EUV optic 128 and ion optics 150) of imaging spectrometer 100 can be controlled statically or dynamically by stage 152.

Figure 16:
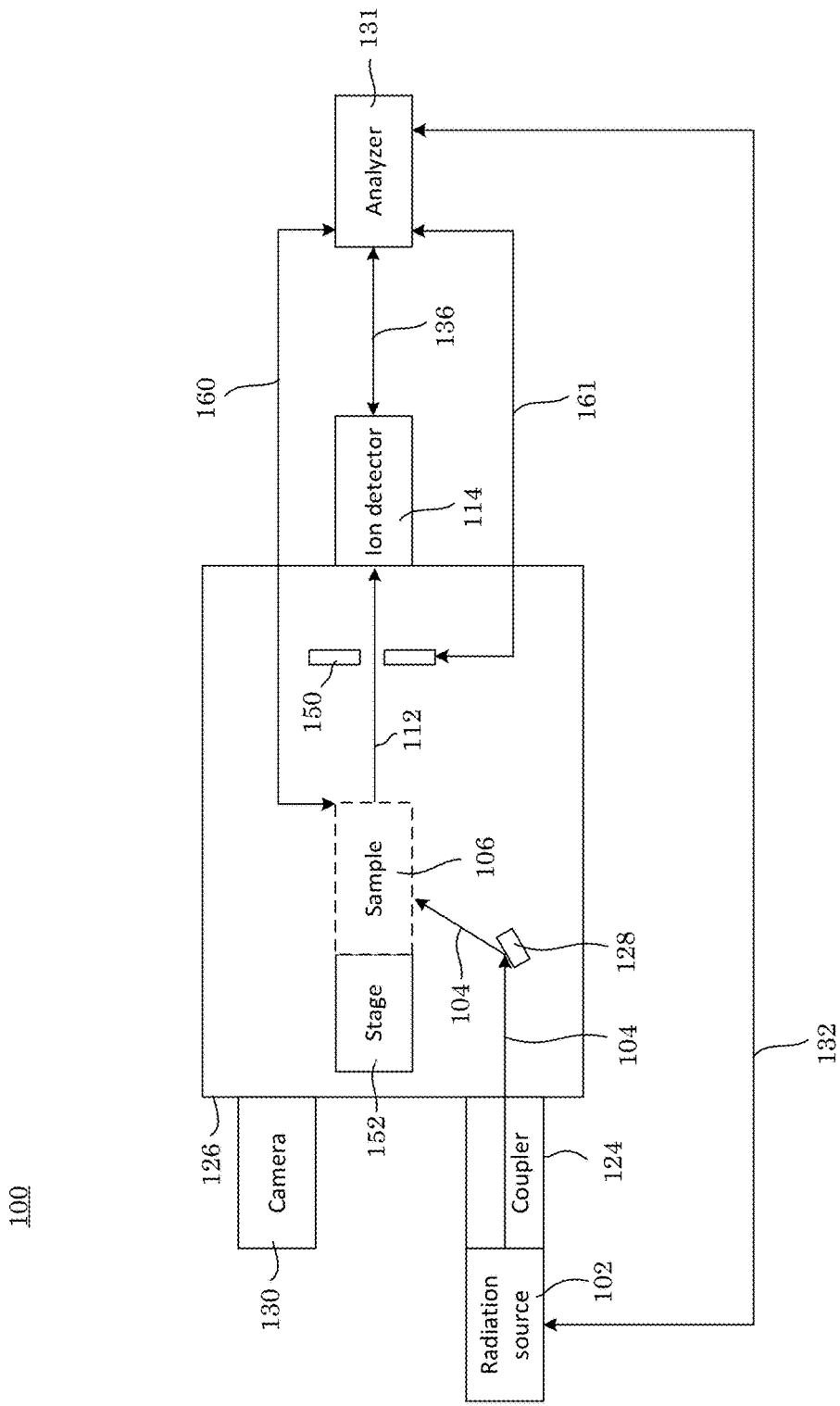
FIG. 16 shows an imaging spectrometer.

According to an embodiment, with reference to FIG. 16, imaging spectrometer 100 includes analyzer 131 to acquire data from ion detector 114, to continuously analyze the data for reconstruction of a shape of sample 106 and a chemical composition of sample 106, and to determine a tomographic shape and composition of sample 106. Here, analyzer 131 can be in electrical communication with radiation source 102 to receive EUV source data 132 (e.g., a pulse length, duty cycle, power, repetition rate, wavelength, and the like of EUV radiation 104) or to control radiation source 102. Analyzer 131 can be in electrical communication with ion detector 114 to receive ion data 136 (e.g., a time-of-arrival, position of arrival on detector 114, energy, two-dimensional image, and the like of photoions 112) or to control ion detector 114 (e.g., detection on time, bias voltage, and the like). Analyzer 131 can be in electrical communication with sample 106 to receive sample data 160 (e.g., temperature, voltage, and the like of sample 106) or to control sample 106 (or stage 152) (e.g., position, bias voltage, and the like). Similarly, analyzer 131 can be in electrical communication with extraction electrode 150 to receive extraction electrode data 161 (e.g., voltage and the like of extraction electrode 150) or to control extraction electrode 150 (e.g., bias voltage and the like).

Figure 17:
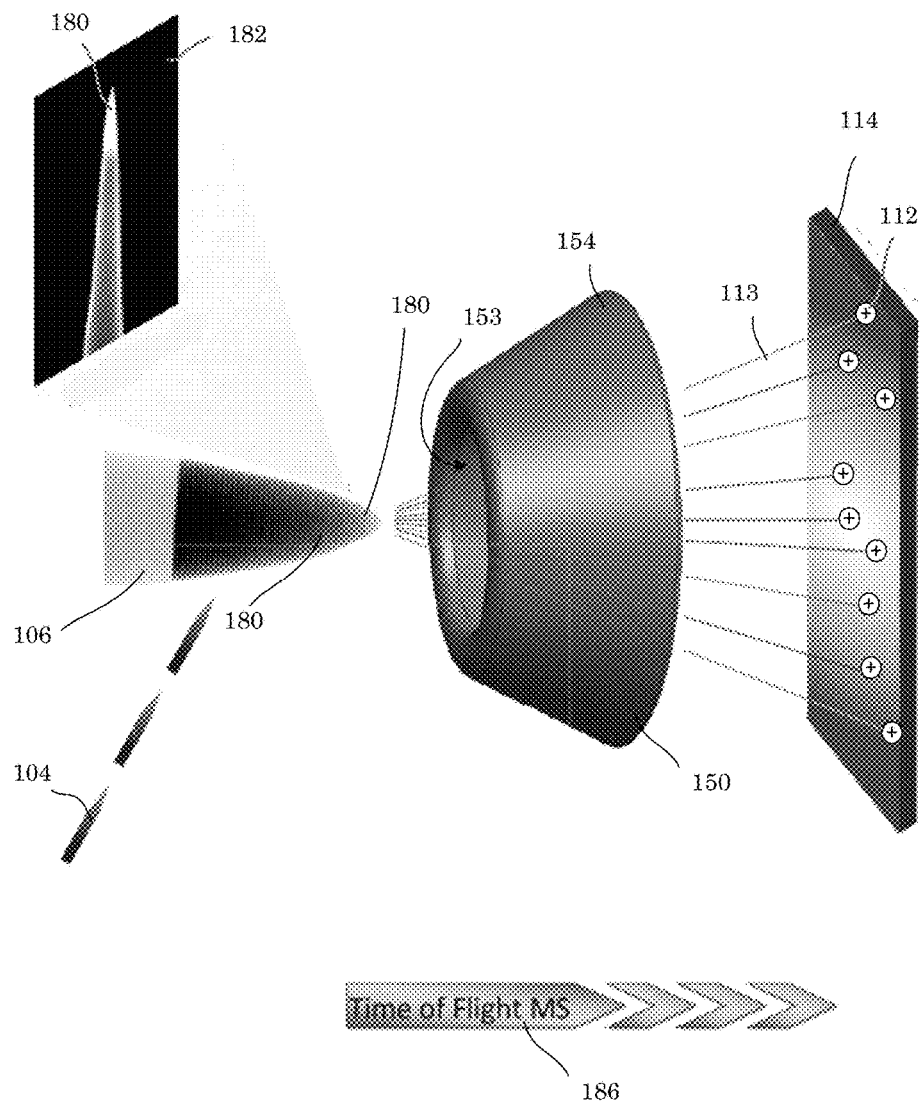
FIG. 17 shows production of photoions images by subjecting a sample to EUV radiation.

Although not shown explicitly in FIG. 13, FIG. 14, FIG. 15, FIG. 16, or FIG. 17, imaging spectrometer 100 can include hardware, instrumentation or software for a fully functional atom probe tomograph. It is contemplated that hardware can include high voltage power supply, timing electronics, and position-sensitive 2D detectors, sample shape and composition reconstruction algorithms, and the like that can be integrated with EUV radiation source 102, EUV optic 128, and other components (e.g., detectors (122, 118, 114) of imaging spectrometer 100 to provide operability of imaging spectrometer 100 as shown in FIG. 17. Here, sample 106 having tip 180 is subjected to pulsed EUV radiation 104 such that photoions 112 are produced from tip 180 and propagate from sample 106 to ion detector 114 along ion trajectory 113. Photoions 112 are communicated through aperture 153 to traverse extraction electrode 150 and impact ion detector 114 (e.g., a two-dimensional particle detector) in a pattern, wherein the position of photoions 112 in the pattern on ion detector 114 depends upon a position of the atoms that were photoionized to produce photoions 112 at tip 180 of sample 106. Photoions 112 propagating in ion trajectories 113 move in ion time-of-flight mass spectrometry direction 186 from sample 106 to ion detector 114. It will be appreciated that production of photoions 112 occurs in a presence of EUV radiation 104.

According to an embodiment, imaging spectrometer 100 includes sample 106 disposed on stage 152 that is disposed in chamber 126. In a certain embodiment, pulsed EUV radiation 104 is from radiation source 102 enters chamber 126 through coupler 124. Pulsed EUV radiation 104 is directed and focused by EUV optics 128 disposed in chamber 126 and is incident upon sample 106. In a certain embodiment, stage 152 adjusts a position of sample 106 with respect to extraction electrode 150. A voltage difference (produced by a bias voltage applied to extraction electrode 150 or sample 106) between extraction electrode 150 and sample 106 provides an electric field therebetween to accelerate and to remove photoions 112 produced in response to EUV radiation 104 of tip 180 of sample 106. Photoions 112 traverse aperture 152 of extraction electrode 150 and impact ion detector 114, e.g., a two-dimensional position-sensitive.

In an embodiment, voltage difference between extraction electrode 150 and sample 106 is selectively adjustable to control a rate of impact of photoions 112 on ion detector 114. A position or focus of EUV radiation 104 incident on sample 106 is selectively adjustable to produce EUV radiation-assisted field evaporation of photoions 112 from sample 106. An interior of chamber 126 has a pressure that can be ultra-high-vacuum provided, e.g., by a vacuum pumping system. The vacuum pumping system can include a vacuum pump such as a titanium sublimation pump, cryogenic, helium refrigerator, diffusion pump, turbo molecular pump, and the like. Optical camera 130 monitors a position or condition of components disposed in chamber 126.

EUV imaging spectrometer 100 includes radiation source 102 to produce EUV radiation 104 for photoionization of atoms of sample 106 to form photoions 112. In an embodiment, radiation source 102 can include a pulsed laser and a gas cell, wherein the gas cell receives a gas that is subjected to pulsed laser light from the pulsed laser to produce EUV radiation 104. Here, EUV radiation 104 can be produced as pulsed light by directing the pulsed laser light into the gas cell that includes a gas such as Kr, Xe, Ar, He, Ne, or a combination thereof. Without wishing to be bound by theory, it is believed that EUV radiation 104 is produced by high harmonic generation of the pulsed laser light by the gas in the gas cell. In an embodiment, pulsed EUV radiation 104 is provided by a high voltage electrical discharge of a gas in a capillary cell. In some embodiments, pulsed EUV radiation 104 is provided by synchrotron radiation. In a particular embodiment, pulsed EUV radiation 104 is produced by a free electron laser.

According to an embodiment, with reference to FIG. 6, radiation source 102 includes pump module 204 to produce pump light 206. Pump module 204 can include host laser 208 that produces host laser light 210 that is communicated from host laser 208 to frequency doubler 212. Pump module 204 receives diode light from laser diode 214, and frequency doubler 212 doubles host laser light 210 (i.e., doubles the energy or halves the wavelength via frequency doubling, e.g., in an optical crystal). Pump light 206 is received by mode-locked laser 218 from pump module 204, wherein mode-locked laser 218 produces laser output 220 that is received by amplifier 226. Amplifier 226 also receives amplifier light 222 from amplifier pump 224 to amplify laser output 220 into pulsed light 228. Pulsed light 228 is communicated from amplifier 226 to high harmonic generator 200. High harmonic generator 200 receives pulsed light 228 and produces EUV radiation 124, which is pulsed.

Here, laser diode 214 can be a laser diode array that produces diode light 216 with an output power and wavelength (e.g., 800 nanometer (nm) continuous wave (CW) radiation with a selected power sufficient to pump host laser 208. Host laser 208 can be, e.g., neodymium (Nd)-doped yttrium aluminum garnet (YAG) laser or other laser that produces host laser light 210 that is CW and has a wavelength at about 1000 nm, although a different laser would provide a different wavelength. Frequency doubler 212 can produce doubled pump light 206, e.g., having CW output and a wavelength of about 500 nm, depending on the wavelength of host laser light 210. Mode-locked laser 218 can be a passively mode-locked laser such as a titanium sapphire (Ti:sapphire) laser to produce laser output 220 having a wavelength, e.g., of about 800 nm with a repetition rate of about 80 MHz.

In an embodiment, coupler 124 receives pulsed EUV radiation 104 from high harmonic generator 200 of radiation source 102 and communicates pulsed EUV radiation 104 chamber 126. Here, an interior of coupler 124 has a pressure that is compatible with propagation of EUV radiation 104 from radiation source 102, e.g., a high harmonic generator 200, to chamber 126. An exemplary pressure of chamber 126 is ultrahigh vacuum. An optical interface between radiation source 102 and coupler 124 can be an EUV optical window (e.g., a metal foil such as an aluminum foil) to transmit EUV radiation 104 therethrough and to transmit EUV radiation 104 into chamber 126.

Disposed in chamber 126 is EUV optic 128 to receive EUV radiation 104 from coupler 124. EUV optics 128 can include mirror 129 and concave reflector 131. Mirror 129 can be a flat mirror, curved EUV mirror, and the like or a combination thereof with concave reflector 131 can have a selected position or angle to adjust EUV radiation 104 with respect to sample 106. It is contemplated that EUV optics 128 (e.g., mirror 129, concave reflector 131, and the like) can focus EUV radiation 104 onto sample 106. In an embodiment, EUV optic 128 is a zone plate to focus EUV radiation 104 on sample 106.

Radiation source 102 can operate at a selected wavelength from 12 nm to 124 nm. The EUV wavelength band provides nearly uniform optical absorption across atoms in sample 106 with absorption depth in sample 106, e.g., of 10 nm. The absorption depth is selectively tunable and can depend upon the wavelength of EUV radiation 104. Moreover, the wavelength of EUV radiation 104 provides efficient photoionization of atoms and photo-disassociation of complex ions. EUV radiation 104 substantially photoionizes elemental species of atoms at tip 180 of sample 106 (see, e.g., a micrograph of sample 106 shown in FIG. 7) and contributes to additional photoionization and disassociation of molecular complexes. As used herein, "EUV light" and "EUV radiation" are identical.

Unexpectedly, surprisingly, and without wishing to be bound by theory, it is believed that a photoionization pathway for field evaporation of ions of sample 106 occurs through photoionization in a presence of EUV radiation 104 and is significantly different than irradiation of sample 106 with a UV wavelength. In conventional use of UV radiation, e.g., in an atom probe microscope, a UV wavelength from 255 nm to 355 nm (corresponding to photon energy from 4.9 eV to 3.5 eV) is less than a photoionization threshold for inorganic solid materials such that substantial photoionization does not occur. In contrast, imaging spectrometer 100 produces EUV radiation 104 with a selected wavelength, e.g., from 12 nm to 124 nm to provide an EUV photon energy, e.g., from 10 eV to 100 eV. In this EUV band, photoionization cross-sections are large, and EUV radiation 104 can singly photoionize or multiply ionize atoms in sample 106 that can include a material of technological interest. EUV radiation 104 can have a substantially uniform optical absorption depth in sample 106, e.g., 10 nm in sample 106, e.g., a metal, plastic, ceramic, polymer, glass, semiconductor, insulator, conductor, hybrid materials composed of such constituents, and the like.

Further, conventional laser atom probes involve thermally-assisted field ion evaporation, wherein field ion evaporation provides removal of atoms from a sample by applying a high electric field (e.g., 10 volts (V)/nm to 60 V/nm) in a presence of UV light that impinges on a sample. In contrast EUV imaging spectrometer 100 includes EUV radiation 104 that photoionizes atoms of sample 106. Instead, EUV imaging spectrometer 100 uses EUV radiation 104 to provide photoionization-assisted field ion evaporation to produce photoions 112 from sample 106 that are produced by electronic excitation. That is, with UV radiation (e.g., 255 nm to 355 nm UV light), thermal pulsing dominates, and significant photoionization does not occur. EUV radiation 104 provides photoionization of constituent atoms of sample 106.

Although photoionization cross-sections can vary among elements of the periodic table, imaging spectrometer 100 with EUV radiation 104 reduces an element-to-element variation in production of photoions 112 compared to conventional atom probe tomography, which employs UV lasers. Element-to-element differences in the field evaporation rate for a conventional pulsed-laser atom probe, in which absorbed pulsed laser light imparts transient increases in temperature of the specimen tip and involves a difference in a zero barrier evaporation field F. Unexpectedly and surprisingly, element-to-element differences in the evaporation rate in imaging spectrometer 100 with pulsed EUV radiation 104 are due to differences in photoionization cross-section because surface species that have been photoionized will generally experience reduced bonding strength to the specimen tip. In thermally assisted pulsing with UV light, the evaporation rate is exponentially dependent on both F and temperature such that changes in applied field F lead to changes in evaporation rate with higher temperature thermal transients yielding greater evaporation rates. Therefore, materials or portions of samples that have relatively reduced UV absorption will yield relatively reduced evaporation rates. For pulsed EUV radiation 104, the contribution to the evaporation rate that is dependent on photoionization is unexpectedly and surprisingly linearly dependent on σ such that element-to-element differences in σ have less influence on the evaporation rate. Additionally, the EUV absorption depth d is unexpectedly and surprisingly comparable or smaller than typical specimen tip diameters for a wide variety of materials of interest, e.g. for 45 eV photons: d=200 nm for Si; d=35 nm for GaAs; d=15 nm for GaN; d=20 nm for Fe; d=35 nm for SiN; d=20 nm for $SiO_2$; d=12 nm for $Al_2O_3$; d=4 nm for $TiO_2$—and so on. Therefore, the thermally-assisted pathway for field evaporation provided by pulsed EUV will generally be far more uniform compared to what is attainable with pulsed UV. Moreover, EUV radiation 104 produces substantially fewer complex ions than UV light, wherein a sample subjected to UV light can produce molecular ions due to thermally-assisted process such as surface diffusion on the sample. EUV radiation 104 provides photoionization and photodissociation of complex ions formed from subjecting sample 106 to EUV radiation 104. As a result, formation of neutral species or complex ions such as molecular ions from sample 106 are substantially absent in a presence of EUV radiation 104 received by sample 106.

Sample 106 is subjected to EUV radiation 104. Photoions 112 are produced from photoionization of atoms of sample 106. Sample 106 can include any material subject to photoionization by EUV radiation 104. Exemplary materials include polymers, glasses, other covalently bonded materials, and the like. Sample 106 can have any shape, e.g., a conical shape, spherical, planar, and the like.

Stage 152 can provide control of a position of sample 106 in chamber 126, in particular with relation to extraction electrode 150. Further, stage 152 can control a temperature of sample 106, remove sample 106 from chamber 126, insert sample 106 into chamber 126 without substantially changing the vacuum level (e.g., the ultrahigh vacuum) of chamber 126, or a combination thereof. Chamber 126 can include additional components such as a load-lock chamber, transfer arm, and the like to manipulate (e.g., move or dispose) extraction electrode 150, sample 106, and the like in chamber 126.

Ion optics, e.g., extraction electrode 150, are disposed proximate to sample 106 and interposed between sample 106 and ion detector 114. In an embodiment, ion optics includes extraction electrode 150. Ion optic 150 includes first end 156 disposed proximate to sample 106 and distal to ion detector 114, second end 158 disposed proximate to ion detector 114 and distal to sample 106, entry aperture 153 through which photoions 112 are transmitted and traverse extraction electrode 150 in electrode interior 164 bounded by wall 154 and exit extraction electrode 150 at exit aperture 152. In an embodiment, the ion optics can include a reflectron disposed to receive photoions 112 transmitted by extraction electrode 150 from sample 106 and to communicate photoions to ion detector by reflecting the photoions in a presence of an electric field in the reflectron.

In an embodiment, extraction electrode 150 receives a bias voltage such that a potential difference exists between extraction electrode 150 in sample 106. Aperture 153 of extraction electrode 150 communicates photoions 112 emitted from sample 106 to ion detector 114. Extraction electrode 150 can be disposed in or removed from chamber 126 without substantially changing the ultra-high vacuum of chamber 126. Imaging spectrometer 100 that includes extraction electrode 150 in combination with sample 106 and ion detector 114 provides acquisition of mass-spectral data and reliable chemical assignments with spatial resolution for mapping materials of sample 106.

Ion detector 114 receives photoions 112 emitted from sample 106. Here, ion detector 114 records arrival of photoions 112, a time taken by photoions 112 to traverse a distance between sample 106 and ion detector 114, a position of arrival on ion detector 114, or a combination thereof. Exemplary ion detectors 114 is a microchannel plate, an electron multiplier modified to detect cations, a Faraday cup, and the like. Exemplary ion detectors also include a those that can record kinetic energy of detected ions and permit determination of the mass of a detected ion. In an embodiment, ion detector 114 is a two-dimensional position-sensitive detector disposed in chamber 126 to detect or record photoions 112 emitted from sample 106 as a function of time-of-arrival based at ion detector 114 and as a function of a position on ion detector 114. Ion detector 114 can include ion optics disposed prior to a detecting surface to steer, focus, pulse, mass select, velocity image, and the like photoions 112. In this manner, ion detector 114 performs time-of-flight mass spectrometry and ion imaging of photoions 112 released from sample 106 in response to sample 106 subjected to EUV radiation 104 that photoionizes atoms of sample 106. From the time of arrival of photoions 112 at ion detector 114 from sample 106, a mass of each photoion 112 can be determine based on the potential difference (i.e., electric field strength) present between sample 106 and extraction electrode 150 when photoions 112 are created. EUV radiation 104 singly photoionizes atoms of sample 106 to produce singly charged photoions 112, and the masses determined from the time-of-flight mass spectrum acquired by ion detector 114 identify the element (i.e., atom) in sample 106 that produced photoions 112. Multiply charged photoions may yield ambiguous assignments since purely time-of-flight detection schemes are sensitive to the ratio on ionic mass divided by ionic charge—hence, multiply charged heavier species may be indistinguishable from singly charged lighter ones. This ambiguity can be eliminated if the detection scheme records both the ionic time-of-flight and the kinetic energy of the detected ion. In such a scheme, the ionic mass can be unequivocally determined. From the position of photoions 112 incident at ion detector 114, a position on sample 106 of the atoms that produced photoions 112 can be determined. The mass of the photoions and the position of the atoms on sample 106 are used in part to determine an elemental composition of sample 106 as a function of position on sample 106. The mass of the photoions in the position of the atoms in sample 106 provide multi-dimensional chemical maps of sample 106. Imaging spectrometer 100 provides near-real-time measurement of a time-varying shape of tip 180 of sample 106 during data acquisition in an absence of dismounting sample 106 or interrupting data acquisition or changing a state of the vacuum in chamber 126.

With reference to FIG. 11, analyzer 131 can include control module 143 and data analysis module 141 interconnected and in electrical communication by data path 135. Control module 143 communicates, controls, monitors, or records functions of and data acquired (e.g., EUV source data 132, ion data 136, sample data 160, extraction electrode data 161, pressure of chamber 126, and the like) by chamber 126, EUV source 102, in-chamber inspection camera 130, ion detector 114, and the like using data path 137.

Data accumulated in control module 143 from sample 106 includes position-sensitive time-of-flight mass spectral information (e.g., ion data 136) and specimen shape information. These data along with other data are communicated to data analysis module 141 in data path 135. Data analysis module 141 analyzes this combined data to determine multi-dimensional chemical maps of sample 106. Control module 143 can include hardware (e.g., a microprocessor and the like), software (e.g., an algorithm, script, or other code) to make the determination of the three-dimensional chemical maps of sample 106.

In an embodiment, a process for making imaging spectrometer 100 includes disposing radiation source 102, coupler 124, and EUV optics 128 on chamber 126 to provide pulsed EUV radiation 104 into chamber 126, to steer and focus EUV radiation 104, and to subject sample 106 to EUV radiation 104; disposing stage 152 in chamber 126 to receive sample 106; disposing extraction electrode 150 and ion detector 114 on chamber 126 such that photoions 114 produced by sample 106 in response to being subjected to EUV radiation 104 and the electric field between sample 106 and extraction electrode 150 are communicated through extraction electrode 150 to ion detector 114 from sample 106 and impact ion detector 114 and a presence a voltage difference between sample 106 and extraction electrode 150.

According to an embodiment, a process for performing imaging spectrometry of sample 106 includes producing, by radiation source 102, EUV radiation 104; subjecting sample 106 to EUV radiation 104; photoionizing a plurality of atoms of sample 104 with EUV radiation 104; forming photoions 112 from the atoms subject to single photoionization by EUV radiation 104; field evaporating photoions 112 from sample 106 in response to sample 106 being subjected to EUV radiation 104 and an electric field between sample 106 and extraction electrode 150; detecting, by ion detector 114, photoions 112: as a function of a time-of-arrival of photoions 112 at ion detector 114 after sample 106 is subjected to EUV radiation 104, or as a function of a position of photoions 112 at ion detector 114; and acquiring, by analyzer 131, data from ion detector 114 to image sample 106. The process can include reconstructing a shape of sample 106; and determining a chemical composition of sample 106 as a function of position in sample 106. The process can include determining a tomographic shape and composition of sample 106. The process can include transmitting, by extraction electrode 150, photoions 112 from sample 106 to ion detector 114, wherein extraction electrode 150 includes aperture 153 to transmit photoions 112, and extraction electrode 150 is disposed proximate to sample 106 and interposed between sample 106 and ion detector 114.

The process also can include applying a potential difference between sample 106 and extraction electrode 150; and increasing the potential difference to detect photoions 112. Sample 106 can be subjected to EUV radiation 104 after the potential difference is increased to form photoions 112; and detecting, by ion detector 114, photoions 112 includes performing time-of-flight mass spectrometry on photoions 112.

According to an embodiment, a process for performing imaging spectrometry on sample 106 includes disposing sample 106 on stage 152; disposed stage 152 and sample 106 in chamber 126; applying a voltage bias between sample 106 and extraction electrode 150; subjecting sample 106 two pulsed EUV radiation 104; optionally monitoring and recording pulsed EUV radiation 104 incident on sample 106; producing photoions 112 in response to subjecting sample 106 to the EUV radiation 104; receiving photoions 112 at ion detector 114; recording a time-of-flight of photoions 112 between sample 106 and ion detector 114 by control module 143; recording the positions upon ion detector 114 at which photoions 112 impact ion detector 114 by control module 143; providing electronic feedback control to control the voltage bias between sample 106 and extraction electrode 150; optionally adjusting the voltage bias to obtain a selected rate of impact of photoions 112 on ion detector 114; optionally providing electronic feedback control to control a selected position or focus of pulsed EUV radiation 104 upon sample 106; adjusting the bias voltage between sample 106 and extraction electrode 150 zero volts (V) at a selected period during data acquisition while EUV radiation 104 is substantially absent at sample 106; terminating the first interval; during a second interval, increasing the voltage bias between sample 106 and extraction electrode 150, subjecting sample 106 to EUV radiation 104, and acquiring time-of-flight mass spectra of photoions 112 and positions of impact of photoions 112 on ion detector 114 to perform imaging spectrometry on sample 106. The alternating cycle between the first interval and the second interval can be performed a plurality of times. During data acquisition, ion time-of-flight data, ion impact positions on ion detector 114, and data associated with other components of imaging spectrometer 100 are acquired by control module 143 or communicated to data analysis module 141 to reconstruct shape and composition of sample 106.

Figure 18:
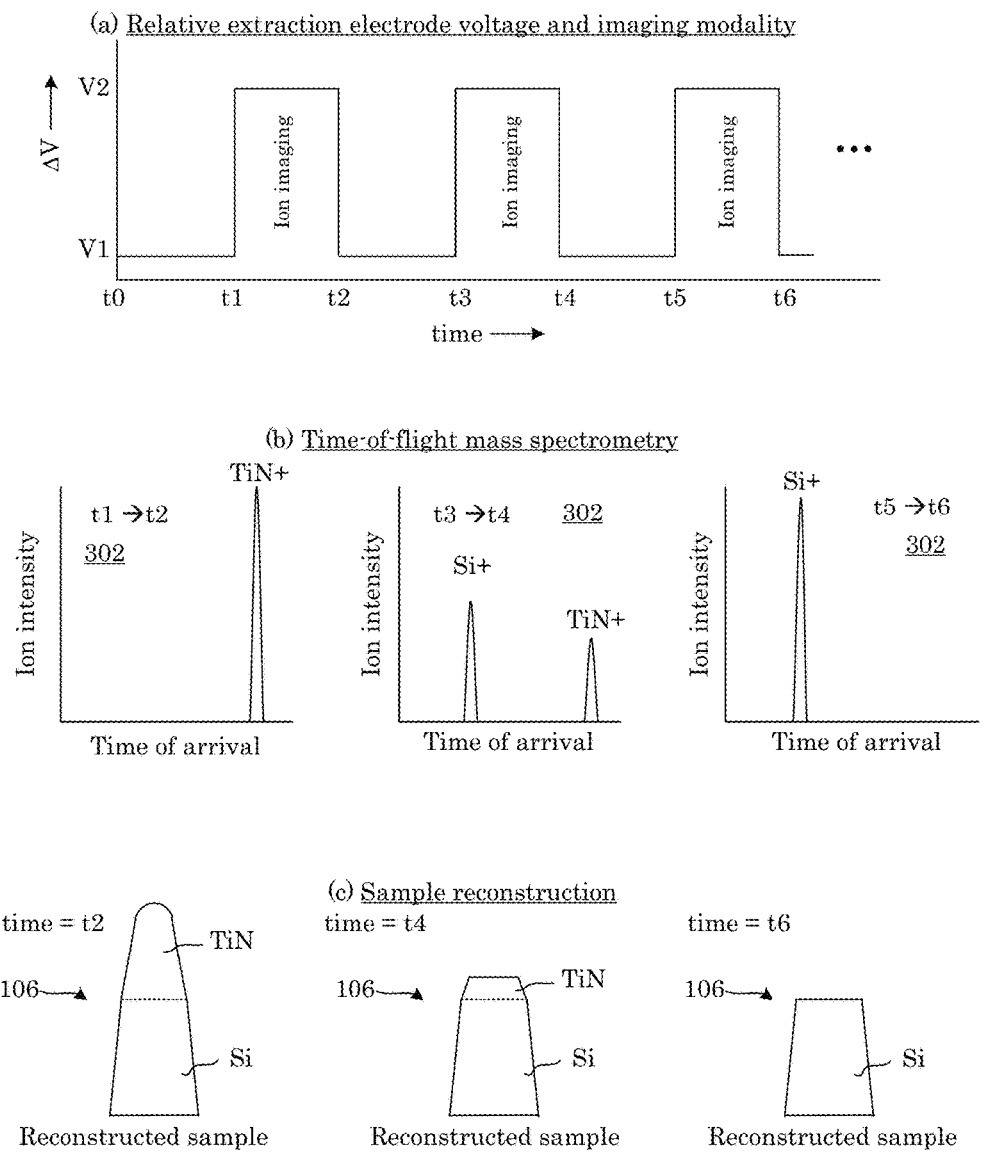
FIG. 18 shows (panel A) a graph of voltage versus time, (panel B) ion time-of-flight (TOF) mass spectra of photoions, and (panel C) reconstruction of a sample.

With reference to FIG. 18, panel A of FIG. 18 shows a graph of the potential difference ΔV between sample 106 and extraction electrode 150 versus time. Between time t0 and time t1, potential difference ΔV is first voltage V1 such that an imaging modality of imaging spectrometer 100 is quiescent imaging, wherein substantially no particles (including ionizing photons) impinge upon sample 106. As shown in panel A of FIG. 18, between time t1 and time t2, potential difference ΔV is second voltage V2 such that an imaging modality of imaging spectrometer 100 is ion imaging, and time-time-of-flight mass spectrometry acquisition occurs, wherein EUV radiation 104 impinges upon sample 106, and ion imaging and detection by ion detector 114 occurs to acquire, e.g., time-of-flight mass spectrometry of photoions 112 emitted from sample 106 as shown in panel B of FIG. 18. At time t2, analyzer 131 can reconstruct the geometrical shape and chemical composition of sample 106 from ion data as shown in panel C of FIG. 18.

As shown in panel A of FIG. 18, between time t2 and time t3, potential difference ΔV is first voltage V1 such that an imaging modality of imaging spectrometer 100 is quiescent imaging. As shown in panel A of FIG. 18, between time t3 and time t4, potential difference ΔV is second voltage V2 such that an imaging modality of imaging spectrometer 100 is ion imaging in which the time-of-flight mass spectrometry acquisition occurs, wherein EUV radiation 104 impinges upon sample 106, and ion imaging and detection by ion detector 114 occurs to acquire, e.g., time-of-flight mass spectrometry of photoions 112 emitted from sample 106 as shown in panel C of FIG. 18. At time t4, analyzer 131 reconstructs the geometrical shape and chemical composition of sample 106 from ion data.

As shown in panel A of FIG. 18, between time t4 and time t5, potential difference ΔV is first voltage V1 such that an imaging modality is quiescent imaging. As shown in panel A of FIG. 18, between time t5 and time t6, potential difference ΔV is second voltage V2 such that an imaging modality is ion imaging and fight mass spectrometry acquisition occurs. At time t6, analyzer 131 reconstructs the geometrical shape and chemical composition of sample 106 from electron data and ion data. Although only three cycles of quiescent imaging, ion imaging, and sample reconstruction are shown in FIG. 18, it should be appreciated that such cycles can be repeated as selected, interrupted, restarted, and the like. Moreover, it is contemplated that sample 106 can be subjected to structural or compositional modification during a cycle or after cycle such that such structural or compositional modification can be ascertained due to electron imaging, ion imaging, or sample reconstruction by imaging spectrometer 100.

In an embodiment, data stored in control module 143 during data acquisition are communicated to data analysis module 141 via data path 135. Data analysis module 141 performs computations to generate three-dimensional chemical maps of sample 106. In performing these computations, data analysis module 141 employs data that includes the shape of sample 106 that is generated using ion times-of-flight between sample 106 and ion detector 114; photoions 112 impact positions on ion detector 114; and the voltage bias between sample 106 and extraction electrode 150.

According to an embodiment, a process for reconstructing the shape and composition of sample 106 includes: during a time interval within which a voltage is applied between sample 106 and extraction electrode 150, subjecting sample 106 to pulsed EUV radiation 104 such that photoions emitted by sample 106 impact positions on detector 114; recording times-of flight of photoions 112; recording the detection sequence of photoions 112 on detector 114; and recording the impact locations of photoions 112 on detector 114. In this manner, a dataset is produced that includes a sequential record of photoions 114 that are identified by their respective times-of-flight. Furthermore, the dataset also includes a record of the positions on the specimen tip of sample 106 from which photoions 112 are emitted as computed using back-projection from respective impact locations on detector 114. A depth of sample 106 at which photoions 112 resided in sample 106 with respect to an initial position of a terminus of tip 181, i.e. before photoions 112 are removed, is determined by starting with the first detected photoion 112 as follow: assigning an equivalent volume to identified photoion 112, wherein the depth increment contributed by this equivalent volume corresponds to the thickness of a thin portion of tip 181 within a field of view of the detector and whose shape and surface area is measured by electron source 108 and detector combinations previously described. Further, in the process, the depth increment is initially assigned as a depth coordinate of the first photoion 112. Then this depth coordinate is corrected by measuring the shape of tip 181 and determining the additional depth increment that must be added given the location on the surface of sample 106 from which photoion 112 was emitted. The process proceeds for successive photoions in a similar fashion eventually identifying the elemental species and original location of each detected photoion from the specimen tip.

The near-real-time measurement of the shape of tip 180 of sample 160 via in-situ imaging by imaging spectrometer 100 provides reconstruction analysis that includes providing dimensional information to analysis algorithms in conjunction with spatial or temporal data from the position-sensitive detectors. Accordingly, data acquisition and analysis can be continuous and performed in an absence of terminating acquisition of data, removing sample 106 from chamber 126, or in other disruption. Beneficially, imaging spectrometer 100 provides accurate calibration for multi-dimensional spatial reconstruction of sample 106. Without wishing to be bound by theory, it is believed that for tip 180 with axial symmetry, a two-dimensional image of tip 180 is sufficient for determination of the chemical image map of sample 106. In an embodiment, axial symmetry of tip 180 is provided during application, e.g. by annular milling in a focused ion beam microscope. As a result, geometry parameters of tip 180 for an accurate three-dimensional spatial reconstruction is provided from two-dimensional electron image.

The imaging spectrometers herein provide numerous beneficial uses such as a metrology instrument to provide accurate, subnanometer three-dimensional chemical mapping of sample 106 with high analytical sensitivity across the periodic table of elements.

Advantageously and unexpectedly, the imaging spectrometers 100 provide acquisition of mass-spectral data and reliable chemical assignments with spatial resolution for mapping samples 106 whose constituent elements may form large molecular ions in embodiments of atom probe tomography tools that employ ion-emission processes that depend upon thermally driven field evaporation. Additionally, the imaging spectrometers 100 provides highly-local structure and chemical composition at interfaces of different materials in sample 106 to determine structure-properties-processing relationship. Further, the imaging spectrometers 100 provide composition and structure at sub-nanometer length scales with high analytical sensitivity and substantially identical detection efficiency across the periodic table of elements. Moreover, imaging spectrometers 100 provide fast, quantitative, easy to interpret, standards-quality chemical composition and three-dimensional geometrical shape of sample 106.

Embodiments of the subject matter and the operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus. Alternatively, or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more computers executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, workstations, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic; magneto-optical disks, optical disks, USB drives, and so on. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The central processing unit and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks). Such interconnects may involve electrical cabling, fiber optics, or be wireless connections.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

The terms "pulsed EUV light" and "pulsed EUV radiation" are identical.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. An extreme ultraviolet (EUV) imaging spectrometer comprising:
a radiation source to:
produce EUV radiation;
subject a sample to the EUV radiation;

sequentially photoionize with the EUV radiation:
  a first atom at a first location from the sample at a first time; and
  a second atom at a second location from the sample at a second time, the first atom and the second atom being field ion evaporated as single atoms from a surface of the sample; and
form photoions from the single atoms subject to photoionization by the EUV radiation, the photoions being radiatively field evaporated from the sample in response to the sample being subjected to the EUV radiation;
an ion detector to detect the photoions:
  as a function of a time-of-arrival of the photoions at the ion detector after the sample is subjected to the EUV radiation; or
  as a function of a position of the photoions at the ion detector.

2. The EUV imaging spectrometer of claim 1, further comprising:
an extraction electrode disposed proximate to the sample and comprising an aperture.

3. The EUV imaging spectrometer of claim 1, further comprising:
a stage to dispose and receive the sample.

4. The EUV imaging spectrometer of claim 1, further comprising:
an analyzer to acquire data from the ion detector.

5. The EUV imaging spectrometer of claim 1, further comprising:
a chamber in which the ion detector is disposed and in which the radiation source is optically coupled,
wherein a pressure of the chamber is an ultrahigh vacuum level when the sample is subjected to the EUV radiation.

6. The EUV imaging spectrometer of claim 1, wherein the radiation source comprises a high harmonic generator, an EUV laser, a synchrotron, or a free electron laser.

7. The EUV imaging spectrometer of claim 1, wherein a wavelength of the EUV radiation is from 10 nanometers (nm) to 124 nm.

8. The EUV imaging spectrometer of claim 1, wherein an EUV absorption length of the EUV radiation by the sample is from sub-nanometer to 500 nanometers.

9. A process for performing extreme ultraviolet (EUV) imaging spectrometry, the process comprising:
producing, by a radiation source, EUV radiation;
subjecting a sample to the EUV radiation;
sequentially photoionizing with the EUV radiation:
  a first atom at a first location from the sample at a first time;
  a second atom at a second location from the sample at a second time, the first atom and the second atom being field ion evaporated as single atoms from a surface of the sample;
forming photoions from the single atoms subject to photoionization by the EUV radiation;
field evaporating the photoions from the sample in response to the sample being subjected to the EUV radiation;
detecting, by an ion detector, the photoions:
  as a function of a time-of-arrival of the photoions at the ion detector after the sample is subjected to the EUV radiation; or
  as a function of a position of the photoions at the ion detector; and
acquiring, by an analyzer, data from the ion detector to image the sample.

10. The process for performing EUV imaging spectrometry of the sample of claim 9, further comprising:
reconstructing a shape of the sample; and
determining a chemical composition of the sample as a function of position in the sample.

11. The process for performing EUV imaging spectrometry of the sample of claim 10, further comprising:
determining a tomographic shape and composition of the sample.

12. The process for performing EUV imaging spectrometry of the sample of claim 9, further comprising:
transmitting, by an extraction electrode, the photoions from the sample to the ion detector,
wherein the extraction electrode comprises an aperture to transmit the photoions, and
the extraction electrode is disposed proximate to the sample and interposed between the sample and the ion detector.

13. The process for performing EUV imaging spectrometry of the sample of claim 12, further comprising:
applying a potential difference between the sample and the extraction electrode; and
increasing the potential difference to detect the photoions.

14. The process for performing EUV imaging spectrometry of the sample of claim 13, wherein the sample is subjected to the EUV radiation after the potential difference is increased to form the photoions; and
detecting, by the ion detector, the photoions comprises performing time-of-flight mass spectrometry on the photoions.

* * * * *